United States Patent
Siddiqui-Jain et al.

(10) Patent No.: US 10,259,835 B2
(45) Date of Patent: Apr. 16, 2019

(54) ALVOCIDIB PRODRUGS HAVING INCREASED BIOAVAILABILITY

(71) Applicant: Tolero Pharmaceuticals, Inc., Lehi, UT (US)

(72) Inventors: Adam Siddiqui-Jain, South Jordan, UT (US); David J. Bearss, Alpine, UT (US)

(73) Assignee: Tolero Pharmaceuticals, Inc., Lehi, UT (US)

( * ) Notice: Subject to any disclaimer, the term of this patent is extended or adjusted under 35 U.S.C. 154(b) by 0 days.

(21) Appl. No.: 15/673,213

(22) Filed: Aug. 9, 2017

(65) Prior Publication Data

US 2017/0334938 A1    Nov. 23, 2017

Related U.S. Application Data

(62) Division of application No. 15/158,206, filed on May 18, 2016, now Pat. No. 9,758,539.

(60) Provisional application No. 62/163,188, filed on May 18, 2015.

(51) Int. Cl.
| | | |
|---|---|---|
| A61K 31/38 | (2006.01) |
| A61P 35/02 | (2006.01) |
| C07D 311/22 | (2006.01) |
| C07D 311/30 | (2006.01) |
| C07D 405/04 | (2006.01) |
| C07F 9/6558 | (2006.01) |

(52) U.S. Cl.
CPC .......... *C07F 9/65586* (2013.01); *A61K 31/38* (2013.01); *A61P 35/02* (2018.01); *C07D 311/22* (2013.01); *C07D 311/30* (2013.01); *C07D 405/04* (2013.01)

(58) Field of Classification Search
CPC ................................ A61K 31/38; A61P 35/02
USPC ................................ 514/217.03, 217.04, 318
See application file for complete search history.

(56) References Cited

U.S. PATENT DOCUMENTS

| | | | |
|---|---|---|---|
| 4,522,811 A | 6/1985 | Eppstein et al. | |
| 4,676,980 A | 6/1987 | Segal et al. | |
| 4,816,567 A | 3/1989 | Cabilly et al. | |
| 4,900,727 A * | 2/1990 | Kattige ................ | C07D 211/42 514/217.03 |
| 4,946,778 A | 8/1990 | Ladner et al. | |
| 5,225,539 A | 7/1993 | Winter | |
| 5,545,806 A | 8/1996 | Lonberg et al. | |
| 5,545,807 A | 8/1996 | Surani et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,674,980 A | 10/1997 | Frankel et al. | |
| 5,804,604 A | 9/1998 | Frankel et al. | |
| 5,916,771 A | 6/1999 | Hon et al. | |
| 5,939,598 A | 8/1999 | Kucherlapati et al. | |
| 5,965,703 A | 10/1999 | Horne et al. | |
| 6,087,366 A | 7/2000 | Park et al. | |
| 6,136,981 A | 10/2000 | Brion et al. | |
| 6,225,473 B1 | 5/2001 | Breipohl et al. | |
| 6,258,540 B1 | 7/2001 | Lo et al. | |
| 6,406,912 B1 | 6/2002 | Holla | |
| 6,576,647 B2 | 6/2003 | Bafus et al. | |
| 6,821,990 B2 | 11/2004 | Kesseler | |
| 7,064,193 B1 | 6/2006 | Cory et al. | |
| 7,714,005 B2 | 5/2010 | Chen et al. | |

(Continued)

FOREIGN PATENT DOCUMENTS

| | | |
|---|---|---|
| CN | 1583776 A | 2/2005 |
| WO | 91/00360 A1 | 1/1991 |

(Continued)

OTHER PUBLICATIONS

Senderowicz, "Flavopiridol: the first cyclin-dependent kinase inhibitor in human clinical trials", Investigational New Drugs, No. 17, No. 3, pp. 313-320 (1999).*

(Continued)

*Primary Examiner* — Kevin E Weddington
(74) *Attorney, Agent, or Firm* — Seed Intellectual Property Law Group LLP

(57) ABSTRACT

Compounds having the following structure (I):

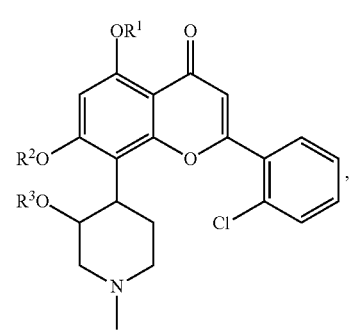

or a stereoisomer, tautomer or pharmaceutically acceptable salt thereof, wherein one of $R^1$, $R^2$ or $R^3$ is —P(=O)(OH)$_2$, and the other two of $R^1$, $R^2$ and $R^3$ are each H, are provided. Pharmaceutical compositions comprising the compounds, and methods for use of the compounds for treating diseases associated with overexpression of a cyclin-dependent kinase (CDK) are also provided.

13 Claims, 13 Drawing Sheets

(56) References Cited

U.S. PATENT DOCUMENTS

| | | |
|---|---|---|
| 7,829,662 B2 | 11/2010 | Korsmeyer et al. |
| 7,868,133 B2 | 1/2011 | Korsemeyer et al. |
| 8,168,755 B2 | 5/2012 | Cardone et al. |
| 8,221,966 B2 | 7/2012 | Letai |
| 9,360,473 B2 | 6/2016 | Cardone |
| 9,540,674 B2 | 1/2017 | Letai |
| 9,758,539 B2 | 9/2017 | Siddiqui-Jain et al. |
| 9,856,303 B2 | 1/2018 | Korsmeyer et al. |
| 9,901,574 B2 | 2/2018 | Warner et al. |
| 9,902,759 B2 | 2/2018 | Korsmeyer et al. |
| 2002/0115613 A1 | 8/2002 | Kumar |
| 2003/0073661 A1 | 4/2003 | Matsuyama et al. |
| 2004/0171809 A1 | 9/2004 | Korsmeyer et al. |
| 2005/0153991 A1 | 7/2005 | Gianella-Borradori et al. |
| 2008/0027105 A1 | 1/2008 | Suarez et al. |
| 2008/0199890 A1 | 9/2008 | Letai |
| 2008/0234201 A1 | 9/2008 | Korsmeyer et al. |
| 2009/0030005 A1 | 1/2009 | Kamb et al. |
| 2010/0286057 A1 | 11/2010 | Walensky et al. |
| 2011/0008371 A1 | 1/2011 | Michelson |
| 2011/0130309 A1 | 6/2011 | Cardone |
| 2011/0154522 A1 | 6/2011 | Korsmeyer et al. |
| 2011/0251240 A1 | 10/2011 | Suarez et al. |
| 2012/0225851 A1 | 9/2012 | Cardone et al. |
| 2013/0079424 A1 | 3/2013 | Gerber et al. |
| 2013/0122492 A1 | 5/2013 | Khosravi et al. |
| 2013/0149718 A1 | 6/2013 | Letai |
| 2014/0080838 A1 | 3/2014 | Wendel et al. |
| 2014/0303167 A1 | 10/2014 | Choidas et al. |
| 2015/0051249 A1 | 2/2015 | Walensky |
| 2015/0150869 A1 | 6/2015 | Cardone et al. |
| 2015/0301053 A1 | 10/2015 | Pierceall et al. |
| 2015/0352097 A1 | 12/2015 | Cardone et al. |
| 2015/0362479 A1 | 12/2015 | Letai et al. |
| 2016/0178612 A1 | 6/2016 | Cardone |
| 2016/0200786 A1 | 7/2016 | Korsmeyer et al. |
| 2016/0231314 A1 | 8/2016 | Ryan et al. |
| 2016/0258933 A1 | 9/2016 | Letai |
| 2016/0273020 A1 | 9/2016 | Pierceall et al. |
| 2016/0303101 A1 | 10/2016 | Warner et al. |
| 2016/0340376 A1 | 11/2016 | Siddiqui-Jain et al. |
| 2017/0184567 A1 | 6/2017 | Letai |
| 2017/0260268 A1 | 9/2017 | Beatty et al. |
| 2018/0172673 A1 | 6/2018 | Bearss et al. |

FOREIGN PATENT DOCUMENTS

| | | |
|---|---|---|
| WO | 92/20373 A1 | 11/1992 |
| WO | 93/08829 A1 | 5/1993 |
| WO | 94/02602 A1 | 2/1994 |
| WO | 94/11026 A2 | 5/1994 |
| WO | 96/15263 A1 | 5/1996 |
| WO | 96/27011 A1 | 9/1996 |
| WO | 96/33735 A1 | 10/1996 |
| WO | 96/34096 A1 | 10/1996 |
| WO | 97/05265 A1 | 2/1997 |
| WO | 99/53049 A1 | 4/1999 |
| WO | 99/53049 A1 | 10/1999 |
| WO | 00/59526 A1 | 10/2000 |
| WO | 01/12661 A2 | 2/2001 |
| WO | 02/20568 A2 | 3/2002 |
| WO | 03/028001 A1 | 4/2003 |
| WO | 03/040168 A2 | 5/2003 |
| WO | 2004/022580 A2 | 3/2004 |
| WO | 2004/058804 A1 | 7/2004 |
| WO | 2005/044839 A2 | 5/2005 |
| WO | 2006/099667 A1 | 9/2006 |
| WO | 2006/101846 A1 | 9/2006 |
| WO | 2007/123791 A2 | 11/2007 |
| WO | 2010/093742 A1 | 8/2010 |
| WO | 2010/147961 A1 | 12/2010 |
| WO | 2011/088137 A2 | 7/2011 |
| WO | 2012/122370 A2 | 9/2012 |
| WO | 2013/082660 A1 | 6/2013 |
| WO | 2013/138702 A2 | 9/2013 |
| WO | 2013/170176 A2 | 11/2013 |
| WO | 2013/188355 A1 | 12/2013 |
| WO | 2013/188978 A1 | 12/2013 |
| WO | 2014/047342 A1 | 3/2014 |
| WO | 2014/066848 A1 | 5/2014 |
| WO | 2015/010094 A1 | 1/2015 |
| WO | 2015/017788 A1 | 2/2015 |
| WO | 2015/042249 A1 | 3/2015 |
| WO | 2015/066305 A1 | 5/2015 |
| WO | 2015/070020 A2 | 5/2015 |
| WO | 2016/061144 A1 | 4/2016 |
| WO | 2016/073913 A1 | 5/2016 |
| WO | 2016/115105 A1 | 7/2016 |
| WO | 2016/149613 A1 | 9/2016 |
| WO | 2016/154380 A1 | 9/2016 |
| WO | 2016/176288 A1 | 11/2016 |
| WO | 2016/176299 A1 | 11/2016 |
| WO | 2017/075349 A1 | 5/2017 |

OTHER PUBLICATIONS

Adams et al., "The Bcl-2 Protein Family: Arbiters of Cell Survival," *Science* 281:1322-1326, 1998.

Adlard et al., "Prediction of the response of colorectal cancer to systemic therapy," *Lancet Oncol.* 3:75-82, 2002.

Aït-Ikhlef et al., "The motoneuron degeneration in the wobbler mouse is independent of the overexpression of a Bcl2 transgene in neurons," *Neuroscience Letters* 199:163-166, 1995.

Almarzooqi et al., "Comparison of Peripheral Blood versus Bone Marrow Blasts Immunophenotype in Pediatric Acute Leukemias," *Ibnosina Journal of Medicine and Biomedical Sciences*, pp. 195-204, 2011. (10 pages).

Altschul et al., "Gapped BLAST and PSI-BLAST: a new generation of protein database search programs," *Nucleic Acids Research* 25(17):3389-3402, 1997.

de Azevedo Jr. et al., "Structural basis for inhibition of cyclin-dependent kinase 9 by flavopiridol," *Biochemical and Biophysical Research Communications* 293:566-571, 2002.

Bae et al., "Underphosphorylated BAD interacts with diverse antiapoptotic Bcl-2 family proteins to regulate apoptosis," *Apoptosis* 6:319-330, 2001.

Barretina et al., "The Cancer Cell Line Encyclopedia enables predictive modelling of anticancer drug sensitivity," *Nature* 483:603-607, 2012; Addendum in: *Nature* 492:290, 2012.

Bearss, "NOXA Priming—Predictive Biomarker for Patients With Acute Myeloid Leukemia to Improve Treatment Outcomes," 2016, retrieved from https://openforum.hbs.org/challenge/precision-medicine/submit-ideas/noxa-priming-predic . . . , 7 pages.

Blachly et al., "Emerging Drug Profile: Cyclin-Dependent Kinase Inhibitors," *Leuk Lymphoma* 54:2133-2143, 2013. (22 pages).

Bodet et al., "BH3-only protein Bik is involved in both apoptosis induction and sensitivity to oxidative stress in multiple myeloma," *British Journal of Cancer* 103:1808-1814, 2010.

Bose et al., "Mcl-1 as a therapeutic target in acute myelogenous leukemia (AML)," *Leukemia Research Reports* 2:12-14, 2013.

Bouillet et al., "Proapoptotic Bcl-2 Relative Bim Required for Certain Apoptotic Responses, Leukocyte Homeostasis, and to Preclude Autoimmunity," *Science* 286:1735-1738, 1999.

Boyd et al., "Bik, a novel death-inducing protein shares a distinct sequence motif with Bcl-2 family proteins and interacts with viral and cellular survival-promoting proteins," *Oncogene* 11:1921-1928, 1995.

Brady et al., "Reflections on a peptide," *Nature* 368:692-693, 1994.

Brennan et al., "Preparation of Bispecific Antibodies by Chemical Recombination of Monoclonal Immunoglobulin $G_1$ Fragments," *Science* 229:81-83, 1985.

Brunelle et al., "MCL-1-dependent leukemia cells are more sensitive to chemotherapy than BCL-2-dependent counterparts," *J. Cell. Biol.* 187(3):429-442, 2009.

Brunetto et al., "First-in-human, Pharmacokinetic and Pharmacodynamic Phase I Study of Resminostat, an Oral Histone Deacetylase Inhibitor, in Patients with Advanced Solid Tumors," *Clin Cancer Res* 19(19):5494-5504, 2013.

(56) References Cited

OTHER PUBLICATIONS

Buggy et al., "CRA-024781: a novel synthetic inhibitor of histone deacetylase enzymes with antitumor activity in vitro and in vivo," *Mol Cancer Ther* 5(5): 1309-1317, 2006.
Buron et al., "Use of Human Cancer Cell Lines Mitochondria to Explore the Mechanisms of BH3 Peptides and ABT-737-Induced Mitochondrial Membrane Permeabilization," *PLoS One* 5(3):e9924, 2010. (13 pages).
Byrd et al., "Flavopiridol Induces Apoptosis in Chronic Lymphocytic Leukemia Cells Via Activation of Caspase-3 Without Evidence of bcl-2 Modulation or Dependence on Functional p53," *Blood* 92:3804-3816, 1998.
Byrd et al., "Sequential Phase II Studies of Flavopiridol by 72-Hour Continuous Infusion and 1-Hour Intravenous Bolus for the Treatment of Relapsed B-Cell Chronic Lymphocytic Leukemia: Results from CALGB Study 19805," *Blood* 104:3485, 2004. (2 pages).
Byrd et al., "Flavopiridol Administered as a Pharmacologically-Derived Schedule Demonstrates Marked Clinical Activity in Refractory, Genetically High Risk, Chronic Lymphocytic Leukemia (CLL)," *Blood* 104:341, 2004. (2 pages).
Byrd et al., "Chronic Lymphocytic Leukemia," *Hematology*, pp. 163-183, 2004. (21 pages).
Byrd et al., "Treatment of Relapsed Chronic Lymphocytic Leukemia by 72-Hour Continuous Infusion or 1-Hour Bolus Infusion of Flavopiridol: Results from Cancer and Leukemia Group B Study 19805," *Clin Cancer Res* 11:4176-4181, 2005.
Byrd et al., "Flavopiridol administered using a pharmacologically derived schedule is associated with marked clinical efficacy in refractory, genetically high-risk chronic lymphocytic leukemia," *Blood* 109:399-404, 2007.
Calin et al., "A MicroRNA Signature Associated with Prognosis and Progression in Chronic Lymphocytic Leukemia," *The New England Journal of Medicine* 353:1793-1801, 2005.
Carlson et al., "Flavopiridol Induces $G_1$ Arrest with Inhibition of Cyclin-dependent Kinase (CDK) 2 and CDK4 in Human Breast Carcinoma Cells," *Cancer Research* 56:2973-2978, 1996.
Caron et al., "Engineered Humanized Dimeric Forms of IgG Are More Effective Antibodies," *J. Exp. Med.* 176:1191-1195, 1992.
Cartron et al., "The First α Helix of Bax Plays a Necessary Role in Its Ligand-Induced Activation by the BH3-Only Proteins Bid and PUMA," *Molecular Cell* 16:807-818, 2004.
Certo et al., "Mitochondria primed by death signals determine cellular addiction to antiapoptotic BCL-2 family members," *Cancer Cell* 9:351-365, 2006.
Chao et al., "Flavopiridol Inhibits P-TEFb and Blocks HIV-1 Replication," *The Journal of Biological Chemistry* 275:28345-28348, 2000.
Chao et al., "Flavopiridol Inactivates P-TEFb and Blocks Most RNA Polymerase II Transcription in Vivo," *The Journal of Biological Chemistry* 276:31793-31799, 2001.
Chen et al., "Caspase cleavage of $Bim_{EL}$ triggers a positive feedback amplification of apoptotic signaling," *PNAS* 101(5): 1235-1240, 2004.
Chen et al., "Mcl-1 Down-regulation Potentiates ABT-737 Lethality by Cooperatively Inducing Bak Activation and Bax Translocation," *Cancer Res* 67(2):782-791, 2007.
Chen et al., "Transcription inhibition by flavopiridol: mechanism of chronic lymphocytic leukemia cell death," *Blood* 106:2513-2519, 2005.
Chen et al., "Differential Targeting of Prosurvival Bcl-2 Proteins by Their BH3-Only Ligands Allows Complementary Apoptotic Function," *Molecular Cell* 17:393-403, 2005.
Chen et al., "Mechanism of action of SNS-032, a novel cyclin-dependent kinase inhibitor in chronic lymphocytic leukemia," *Blood* 113:4637-4645, 2009.
Cheng et al., "Bax-independent inhibition of apoptosis by $Bcl-x_L$," *Nature* 379:554-556, 1996.
Cheng et al., "BCL-2, $BCL-X_L$ Sequester BH3 Domain-Only Molecules Preventing BAX- and BAK-Mediated Mitochondrial Apoptosis," *Molecular Cell* 8:705-711, 2001.
Cheson et al., "National Cancer Institute-Sponsored Working Group Guidelines for Chronic Lymphocytic Leukemia: Revised Guidelines for Diagnosis and Treatment," *Blood* 87:4990-4997, 1996.
Chipuk et al., "Direct Activation of Bax by p53 Mediates Mitochondrial Membrane Permeabilization and Apoptosis," *Science* 303:1010-1014, 2004.
Chittenden et al., "A conserved domain in Bak, distinct from BH1 and BH2, mediates cell death and protein binding functions," *The EMBO Journal* 14(22):5589-5596, 1995.
Chittenden et al., "Induction of apoptosis by the Bcl-2 homologue Bak," *Nature* 374:733-736, 1995.
Chonghaile et al., "Mitochondrial Apoptotic Priming Measured by BH3 Profiling Regulates Clinical Response to Chemotherapy in Myeloma and Acute Lymphoblastic Leukemia and Explains Therapeutic Index," *Blood* 118:1442, 2011. (6 pages).
Chonghaile et al., "Pretreatment Mitochondrial Priming Correlates with Clinical Response to Cytotoxic Chemotherapy," *Science* 334:1129-1133, 2011.
Chonghaile et al., "Supporting Online Material for: Pretreatment Mitochondrial Priming Correlates with Clinical Response to Cytotoxic Chemotherapy," *Science* 334:1129-1133, 2011. (36 pages).
Chonghaile et al., "Mimicking the BH3 domain to kill cancer cells," *Oncogene* 27:S149-S157, 2009.
Choudhary et al., "MCL-1 and BCL-xL-dependent resistance to the BCL-2 inhibitor ABT-199 can be overcome by preventing PI3K/AKT/mTOR activation in lymphoid malignancies," *Cell Death and Disease* 6:e1593, 2015. (12 pages).
Cole et al., "The EBV-Hybridoma Technique and Its Application to Human Lung Cancer," in Reisfeld et al. (eds.), *Monoclonal Antibodies and Cancer Therapy*, Alan R. Liss, Inc., New York, New York, USA, 1985, pp. 77-96.
Conaway et al., "The Mediator Complex and Transcription Elongation," *Biochim Biophys Acta* 1829:69-75, 2013. (16 pages).
Cory et al., "The BCL2 Family: Regulators of the Cellular Life-Or-Death Switch," *Nature Reviews Cancer* 2:647-656, 2002.
Cosulich et al., "Regulation of apoptosis by BH3 domains in a cell-free system," *Current Biology* 7:913-920, 1997.
Cote et al., "Generation of human monoclonal antibodies reactive with cellular antigens," *Proc. Natl. Acad. Sci. USA* 80:2026-2030, 1983.
Czabotar et al., "Bax activation by Bim?" *Cell Death and Differentiation* 16:1187-1191, 2009.
Czabotar et al., "Structural insights into the degradation of Mcl-1 induced by BH3 domains," *PNAS* 104:6217-6222, 2007.
Czech et al., "Antitumoral activity of flavone L 86-8275," *International Journal of Oncology* 6:31-36, 1995.
Daigle et al., "Potent inhibition of DOT1L as treatment of MLL-fusion leukemia," *Blood* 122(6):1017-1025, 2013.
Danial et al., "Cell Death: Critical Control Points," *Cell* 116:205-219, 2004.
Davids et al., "BH3 Profiling Demonstrates That Restoration of Apoptotic Priming Contributes to Increased Sensitivity to PI3K Inhibition in Stroma-Exposed Chronic Lymphocytic Leukemia Cells," *Blood* 118:974, 2011. (6 pages).
Davids et al., "Targeting the B-Cell Lymphoma/Leukemia 2 Family in Cancer," *Journal of Clinical Oncology* 30(25):3127-3135, 2012.
Degrado, "Design of Peptides and Proteins," *Advances in Protein Chemistry* 39:51-124, 1988.
Deng et al., "BH3 Profiling Identifies Three Distinct Classes of Apoptotic Blocks to Predict Response to ABT-737 and Conventional Chemotherapeutic Agents," *Cancer Cell* 12:171-185, 2007.
Derenne et al., "Antisense strategy shows that Mcl-1 rather than Bcl-2 or $Bcl-x_L$ is an essential survival protein in human myeloma cells," *Blood* 100:194-199, 2002.
Desagher et al., "Bid-induced Conformational Change of Bax Is Responsible for Mitochondrial Cytochrome c Release during Apoptosis," *The Journal of Cell Biology* 144(5):891-901, 1999.
Dettman et al., "Context Dependent Diagnosis Test for Guiding Cancer Treatment," U.S. Appl. No. 62/102,499, filed Jan. 12, 2015, 71 pages.

(56) References Cited

OTHER PUBLICATIONS

Dettman et al., "Abstract 3400: Mitochondrial profiling in AML patients treated with an Alvocidib containing regimen reveals MCL1 dependency in responder bone marrow," *Cancer Res* 75:3400, 2015. (2 pages).

Di Lisa et al., "Mitochondrial Function and Cell Injury in Single Cardiac Myocytes Exposed to Anoxia and Reoxygenation," *Transplantation Proceedings* 27(5):2829-2830, 1995.

Di Lisa et al., "Mitochondrial membrane potential in single living adult rat cardiac myocytes exposed to anoxia or metabolic inhibition," *Journal of Physiology* 486.1:1-13, 1995.

Diamandis et al. (eds.), *Immunoassay*, Academic Press, San Diego, CA, 1996, 613 pages.

Dinnen et al., "Redirecting Apoptosis to Aponecrosis Induces Selective Cytotoxicity to Pancreatic Cancer Cells through Increased ROS, Decline in ATP Levels, and VDAC," *Mol Cancer Ther* 12(12):2792-2803, 2013.

Döhner et al., "Genomic Aberrations and Survival in Chronic Lymphocytic Leukemia," *The New England Journal of Medicine* 343:1910-1916, 2000.

Egle et al., "Bim is a suppressor of Myc-induced mouse B cell leukemia," *PNAS* 101(16):6164-6169, 2004.

Ellerby et al., "Anti-cancer activity of targeted pro-apoptotic peptides," *Nature Medicine* 5(9):1032-1038, 1999.

Elliott et al., "Intercellular Trafficking and Protein Delivery by a Herpesvirus Structural Protein," *Cell* 88:223-233, 1997.

Elston et al., "Pathological prognostic factors in breast cancer. I. The value of histological grade in breast cancer: experience from a large study with long-term follow-up," *Histopathology* 19:403-410, 1991.

Ember et al., "Acetyl-lysine Binding Site of Bromodomain-Containing Protein 4 (BRD4) Interacts with Diverse Kinase Inhibitors," *ACS Chem. Biol.* 9:1160-1171, 2014.

Eskes et al., "Bid Induces the Oligomerization and Insertion of Bax into the Outer Mitochondrial Membrane," *Molecular and Cellular Biology* 20(3):929-935, 2000.

Falkenberg et al., "Histone deacetylases and their inhibitors in cancer, neurological diseases and immune disorders," *Nature Reviews Drug Discovery* 13:673-691, 2014.

Fanidi et al., "Cooperative interaction between c-myc and bcl-2 proto-oncogenes," *Nature* 359:554-556, 1992.

Filippakopoulos et al., "Selective inhibition of BET bromodomains," *Nature* 468:1067-1073, 2010.

Filippakopoulos et al., "Targeting bromodomains: epigenetic readers of lysine acetylation," *Nature Reviews Drug Discovery* 13:337-356, 2014.

Fish et al., "Identification of a Chemical Probe for Bromo and Extra C-Terminal Bromodomain Inhibition through Optimization of a Fragment-Derived Hit," *J. Med. Chem.* 55:9831-9837, 2012.

Fiskum et al., "[21] Apoptosis-Related Activities Measured with Isolated Mitochondria and Digitonin-Permeabilized Cells," *Methods in Enzymology* 322:222-234, 2000.

Fiskus et al., "Highly Active Combination of BRD4 Antagonist and Histone Deacetylase Inhibitor against Human Acute Myelogenous Leukemia Cells," *Molecular Cancer Therapeutics* 13:1142-1154, 2014.

Flinn et al., "Flavopiridol administered as a 24-hour continuous infusion in chronic lymphocytic leukemia lacks clinical activity," *Leukemia Research* 29:1253-1257, 2005.

Foight et al., "Designed BH3 Peptides with High Affinity and Specificity for Targeting Mcl-1 in Cells," *ACS Chem. Biol.* 9:1962-1968, 2014.

Frankel et al., "Activity of synthetic peptides from the Tat protein of human immunodeficiency virus type 1," *Proc. Natl. Acad. Sci. USA* 86:7397-7401, 1989.

Friedman et al., "Precision medicine for cancer with next-generation functional diagnostics," *Nat Rev Cancer* 15(12):747-756, 2015. (26 pages).

Fuchs et al., "Pathway for Polyarginine Entry into Mammalian Cells," *Biochemistry* 43(9):2438-2444, 2004. (15 pages).

Fukui et al., "The Analysis of the Effect of JQ1 and Flavopiridol on Chondrocytes under Inflammatory Stimuli," *ORS 2014 Annual Meeting*, New Orleans, Louisiana, USA, Mar. 15-18, 2014, 4 pages.

Futaki et al., "Arginine-rich Peptides: An Abundant Source of Membrane-Permeable Peptides Having Potential as Carriers for Intracellular Protein Delivery," *The Journal of Biological Chemistry* 276(8):5836-5840, 2001.

Geserick et al., "The ratio of Mcl-1 and Noxa determines ABT737 resistance in squamous cell carcinoma of the skin," *Cell Death and Disease* 5:e1412, 2014. (14 pages).

Giles et al., "A Phase I Study of Intravenous LBH589, a Novel Cinnamic Hydroxamic Acid Analogue Histone Deacetylase Inhibitor, in Patients with Refractory Hematologic Malignancies," *Clin Cancer Res* 12(15):4628-4635, 2006.

Gojo et al., "The Cyclin-dependent Kinase Inhibitor Flavopiridol Induces Apoptosis in Multiple Myeloma Cells through Transcriptional Repression and Down-Regulation of Mcl-1," *Clinical Cancer Research* 8:3527-3538, 2002.

Goldsmith et al., "BH3 peptidomimetics potently activate apoptosis and demonstrate single agent efficacy in neuroblastoma," *Oncogene* 25:4525-4533, 2006.

Göttlicher et al., "Valproic acid defines a novel class of HDAC inhibitors inducing differentiation of transformed cells," *The EMBO Journal* 20(24):6969-6978, 2001.

Green, "Life, Death, BH3 Profiles, and the Salmon Mousse," *Cancer Cell* 12:97-99, 2007.

Green et al., "A matter of life and death," *Cancer Cell* 1:19-30, 2002.

Green et al., "The Pathophysiology of Mitochondrial Cell Death," *Science* 305:626-629, 2004.

Griffiths et al., "Cell Damage-induced Conformational Changes of the Pro-Apoptotic Protein Bak In Vivo Precede the Onset of Apoptosis," *The Journal of Cell Biology* 144(5):903-914, 1999.

Gross et al., "Enforced dimerization of BAX results in its translocation, mitochondrial dysfunction and apoptosis," *The EMBO Journal* 17(14):3878-3885, 1998.

Gruber et al., "Efficient Tumor Cell Lysis Mediated by a Bispecific Single Chain Antibody Expressed in *Escherichia coli,*" *Journal of Immunology* 152:5368-5374, 1994.

Guha, "Cyclin-dependent kinase inhibitors move into Phase III," *Nature Reviews Drug Discovery* 11:892-894, 2012.

Gul et al., "Apoptotic blocks and chemotherapy resistance: strategies to identify Bcl-2 protein signatures," *Briefings in Functional Genomics and Proteomics* 7(1):27-34, 2008.

Hanahan, "Heritable formation of pancreatic β-cell tumours in transgenic mice expressing recombinant insulin/simian virus 40 oncogenes," *Nature* 315:115-122, 1985.

Hanahan et al., "The Hallmarks of Cancer," *Cell* 100:57-70, 2000.

Hans et al., "β-Carbolines induce apoptosis in cultured cerebellar granule neurons via the mitochondrial pathway," *Neuropharmacology* 48:105-117, 2005.

Harada et al., "Survival factor-induced extracellular signal-regulated kinase phosphorylates BIM, inhibiting its association with BAX and proapoptotic activity," *PNAS* 101(43):15313-15317, 2004.

Hemann et al., "Suppression of tumorigenesis by the p53 target PUMA," *PNAS* 101(25):9333-9338, 2004.

Hemann et al., "Evasion of the p53 tumour surveillance network by tumour-derived MYC mutants," *Nature* 436(7052):807-811, 2005. (13 pages).

Hengartner et al., "C. elegans Cell Survival Gene ced-9 Encodes a Functional Homolog of the Mammalian Proto-Oncogene bcl-2," *Cell* 76:665-676, 1994.

Hirst et al., "Application of Non-Parametric Regression to Quantitative Structure-Activity Relationships," *Bioorganic & Medicinal Chemistry* 10:1037-1041, 2002.

Hnisz et al., "Super-Enhancers in the Control of Cell Identity and Disease," *Cell* 155:934-947, 2013.

Holinger et al., "Bak BH3 Peptides Antagonize Bcl-$x_L$ Function and Induce Apoptosis through Cytochrome c-independent Activation of Caspases," *The Journal of Biological Chemistry* 274(19):13298-13304, 1999.

Holliger et al., "'Diabodies': Small bivalent and bispecific antibody fragments," *Proc. Natl. Acad. Sci. USA* 90:6444-6448, 1993.

(56) References Cited

OTHER PUBLICATIONS

Hoogenboom et al., "By-passing Immunisation—Human Antibodies from Synthetic Repertoires of Germline $V_H$ Gene Segments Rearranged in Vitro," *J. Mol. Biol.* 227:381-388, 1992.

Hopp et al., "Prediction of protein antigenic determinants from amino acid sequences," Proc. Natl. Acad. Sci. USA 78(6):3824-3828, 1981.

Hoppel et al., "The Action of Digitonin on Rat Liver Mitochondria," *Biochem J.* 107:367-375, 1968.

Hsu et al., "Nonionic Detergents Induce Dimerization among Members of the Bcl-2 Family," *The Journal of Biological Chemistry* 272(21):13829-13834, 1997.

Huang et al., "BH3-Only Proteins—Essential Initiators of Apoptotic Cell Death," *Cell* 103:839-842, 2000.

Huse et al., "Generation of a Large Combinatorial Library of the Immunoglobulin Repertoire in Phage Lambda," *Science* 246:1275-1281, 1989.

Innocenti et al., "Flavopiridol Metabolism in Cancer Patients Is Associated with the Occurrence of Diarrhea," *Clinical Cancer Research* 6:3400-3405, 2000.

Inohara et al., "harakiri, a novel regulator of cell death, encodes a protein that activates apoptosis and interacts selectively with survival-promoting proteins Bcl-2 and Bcl-$X_L$," *The EMBO Journal* 16(7):1686-1694, 1997.

Ishizawa et al., "Mitochondrial Profiling of Acute Myeloid Leukemia in the Assessment of Response to Apoptosis Modulating Drugs," *PLoS One* 10(9):e0138377, 2015. (16 pages).

Jackson et al., "Heat shock induces the release of fibroblast growth factor 1 from NIH 3T3 cells," *Proc. Natl. Acad. Sci. USA* 89:10691-10695, 1992.

Jameson et al., "A rationally designed CD4 analogue inhibits experimental allergic encephalomyelitis," *Nature* 368:744-746, 1994.

Jones et al., "Replacing the complementarity-determining regions in a human antibody with those from a mouse," *Nature* 321:522-525, 1986.

Jonkers et al., "Oncogene addiction: Sometimes a temporary slavery," *Cancer Cell* 6:535-538, 2004.

Kasper et al., "Targeting MCL-1 sensitizes FLT3-ITD-positive leukemias to cytotoxic therapies," *Blood Cancer J* 2: 10 pages, 2012.

Keating et al., "Results of First Salvage Therapy for Patients Refractory to a Fludarabine Regimen in Chronic Lymphocytic Leukemia," *Leukemia and Lymphoma* 43(9):1755-1762, 2002.

Keating et al., "Therapeutic role of alemtuzumab (Campath-1H) in patients who have failed fludarabine: results of a large international study," *Blood* 99:3554-3561, 2002.

Kelekar et al., "Bcl-2-family proteins: the role of the BH3 domain in apoptosis," *Trends in Cell Biology* 8:324-330, 1998.

Kelekar et al., "Bad Is a BH3 Domain-Containing Protein That Forms an Inactivating Dimer with Bcl-$X_L$," *Molecular and Cellular Biology* 17(12):7040-7046, 1997.

KG-1, ATCC® CCL-246™, ATCC Product Sheet, May 31, 2013, 3 pages.

Kitada et al., "Protein kinase inhibitors flavopiridol and 7-hydroxystaurosporine down-regulate antiapoptosis proteins in B-cell chronic lymphocytic leukemia," *Blood* 96:393-397, 2000.

Köhler et al., "Continuous cultures of fused cells secreting antibody of predefined specificity," *Nature* 256:495-497, 1975.

König et al., "The Novel Cyclin-Dependent Kinase Inhibitor Flavopiridol Downregulates Bcl-2 and Induces Growth Arrest and Apoptosis in Chronic B-Cell Leukemia Lines," *Blood* 90:4307-4312, 1997.

Korsmeyer et al., "Pro-apoptotic cascade activates BID, which oligomerizes BAK or BAX into pores that result in the release of cytochrome c," *Cell Death and Differentiation* 7:1166-1173, 2000.

Kozbor et al., "The production of monoclonal antibodies from human lymphocytes," *Immunology Today* 4(3):72-79, 1983.

Kryštof et al., "Cyclin-Dependent Kinase Inhibitors as Anticancer Drugs," *Current Drug Targets* 11:291-302, 2010.

Kuwana et al., "Bid, Bax, and Lipids Cooperate to Form Supramolecular Openings in the Outer Mitochondrial Membrane," *Cell* 111:331-342, 2002.

Kuwana et al., "BH3 Domains of BH3-Only Proteins Differentially Regulate Bax-Mediated Mitochondrial Membrane Permeabilization Both Directly and Indirectly," *Molecular Cell* 17:525-535, 2005.

Kyte et al., "A Simple Method for Displaying the Hydropathic Character of a Protein," *J. Mol. Biol.* 157:105-132, 1982.

La Vieira et al., "Cell permeable BH3-peptides overcome the cytoprotective effect of Bcl-2 and Bcl-$X_L$," *Oncogene* 21:1963-1977, 2002.

Labi et al., "Targeting the Bcl-2-regulated apoptosis pathway by BH3 mimetics: a breakthrough in anticancer therapy?," *Cell Death and Differentiation* 15:977-987, 2008.

Leo et al., "Characterization of the Antiapoptotic Bcl-2 Family Member Myeloid Cell Leukemia-1 (Mcl-1) and the Stimulation of Its Message by Gonadotropins in the Rat Ovary," *Endocrinology* 140(12):5469-5477, 1999.

Letai, "The BCL-2 network: Mechanistic insights and therapeutic potential," *Drug Discovery Today: Disease Mechanisms* 2(2):145-151, 2005.

Letai et al., "Antiapoptotic BCL-2 is required for maintenance of a model leukemia," *Cancer Cell* 6:241-249, 2004.

Letai, "Perturbing cancer cell mitochondria to learn how to kill cancer with BH3 profiling," Dana-Farber Cancer Institute, Broad Institute, *Cell Circuits and Epigenomics*, Jul. 28, 2014, 47 pages.

Letai, "BH3 domains as BCL-2 inhibitors: prototype cancer therapeutics," *Expert Opin. Biol. Ther.* 3:293-304, 2003.

Letai et al., "Distinct BH3 domains either sensitize or activate mitochondrial apoptosis, serving as prototype cancer therapeutics," *Cancer Cell* 2:183-192, 2002.

Li et al., "tsg101: A Novel Tumor Susceptibility Gene Isolated by Controlled Homozygous Functional Knockout of Allelic Loci in Mammalian Cells," *Cell* 85:319-329, 1996.

Li et al., "Cleavage of BID by Caspase 8 Mediates the Mitochondrial Damage in the Fas Pathway of Apoptosis," *Cell* 94:491-501, 1998.

Li et al., "Endonuclease G is an apoptotic DNase when released from mitochondria," *Nature* 412:95-99, 2001.

Lin et al., "Seventy-Two Hour Continuous Infusion Flavopiridol in Relapsed and Refractory Mantle Cell Lymphoma," *Leukemia & Lymphoma* 43:793-797, 2002.

Lin et al., "Flavopiridol given as a 30-min intravenous (IV) bolus followed by 4-hr continuous IV infusion (CIVI) results in clinical activity and tumor lysis in refractory chronic lymphocytic leukemia (CLL)," *Journal of Clinical Oncology, 2004 ASCO Annual Meeting Proceedings (Post-Meeting Edition)* 22(14S):8564, 2004. (1 page).

Liu et al., "Bax conformational change is a crucial step for PUMA-mediated apoptosis in human leukemia," *Biochemical and Biophysical Research Communications* 310:956-962, 2003.

Liu et al., "BH3-based Fusion Artificial Peptide Induces Apoptosis and Targets Human Colon Cancer," *Molecular Therapy* 17:1509-1516, 2009.

Liu et al., "CDKI-71, a novel CDK9 inhibitor, is preferentially cytotoxic to cancer cells compared to flavopiridol," *Int. J. Cancer* 130:1216-1226, 2012.

Lonberg et al., "Antigen-specific human antibodies from mice comprising four distinct genetic modifications," *Nature* 368:856-859, 1994.

Long et al., "Optimization and validation of mitochondria-based functional assay as a useful tool to identify BH3-like molecules selectively targeting anti-apoptotic Bcl-2 proteins," *BMC Biotechnology* 13:45, 2013. (10 pages).

Lovén et al., "Selective Inhibition of Tumor Oncogenes by Disruption of Super-Enhancers," *Cell* 153:320-334, 2013. (27 pages).

Lozanski et al., "Alemtuzumab is an effective therapy for chronic lymphocytic leukemia with p53 mutations and deletions," *Blood* 103:3278-3281, 2004.

Luo et al., "Bid, a Bcl2 Interacting Protein, Mediates Cytochrome c Release from Mitochondria in Response to Activation of Cell Surface Death Receptors," *Cell* 94:481-490, 1998.

Lutter et al., "The pro-apoptotic Bcl-2 family member tBid localizes to mitochondrial contact sites," *BMC Cell Biology* 2:22, 2001. (9 pages).

(56) References Cited

OTHER PUBLICATIONS

Marani et al., "Identification of Novel Isoforms of the BH3 Domain Protein Bim Which Directly Activate Bax to Trigger Apoptosis," *Molecular and Cellular Biology* 22(11):3577-3589, 2002.

Marks et al., "By-passing Immunization: Human Antibodies from V-gene Libraries Displayed on Phage,"*J. Mol. Biol.* 222:581-597, 1991.

Marks et al., "By-Passing Immunization: Building High Affinity Human Antibodies By Chain Shuffling," *Nature Bio/Technology* 10:779-783, 1992.

Martin, "Opening the Cellular Poison Cabinet," *Science* 330:1330-1331, 2010.

Mason et al., "The Hypogonadal Mouse: Reproductive Functions Restored by Gene Therapy," *Science* 234:1372-1378, 1986.

Matsushita et al., "A High-Efficiency Protein Transduction System Demonstrating the Role of PKA in Long-Lasting Long-Term Potentiation," *The Journal of Neuroscience* 21(16):6000-6007, 2001.

Matsuzaki, "Why and how are peptide-lipid interactions utilized for self defence?," *Biochem. Soc. Transactions* 29:598-601, 2001.

McDonnell et al., "bcl-2-Immunoglobulin Transgenic Mice Demonstrate Extended B Cell Survival and Follicular Lymphoproliferation," *Cell* 57:79-88, 1989.

Means et al., *Chemical Modification of Proteins*, Holden-Day, Inc., San Francisco, California, USA, 1974, "Modifications to change properties," Chapter 3, pp. 35-54. (22 pages)

Miller et al., "Therapeutic Strategies to Enhance the Anticancer Efficacy of Histone Deacetylase Inhibitors," *Journal of Biomedicine and Biotechnology* 2011 :514261, 2011. (17 pages)

Milstein et al., "Hybrid hybridomas and their use in immunohistochemistry," *Nature* 305:537-540, 1983.

Molassiotis et al., "Use of complementary and alternative medicine in cancer patients: A European Survery," *Annals of Oncology* 16:655-663, 2005.

Montero et al., "Drug-Induced Death Signaling Strategy Rapidly Predicts Cancer Response to Chemotherapy," *Cell* 160:977-989, 2015. (14 pages).

Moore et al., "Chronic lymphocytic leukemia requires BCL2 to sequester prodeath BIM, explaining sensitivity to BCL2 antagonist ABT-737," *The Journal of Clinical Investigation* 117(1): 112-121, 2007.

Moore et al., "BH3 profiling—measuring integrated function of the mitochondrial apoptotic pathway to predict cell fate decisions," *Cancer Lett* 332:202-205, 2013. (10 pages).

Morrison, "Success in specification," *Nature* 368:812-813, 1994.

Muchmore et al., "X-ray and NMR structure of human Bcl-$x_L$, an inhibitor of programmed cell death," *Nature* 381:335-341, 1996. (16 pages).

Munson et al., "LIGAND: A Versatile Computerized Approach for Characterization of Ligand-Binding Systems," *Analytical Biochemistry* 107:220-239, 1980. (22 pages).

Murthi et al., "Structure-Activity Relationship Studies of Flavopiridol Analogues," *Bioorganic & Medicinal Chemistry Letters* 10:1037-1041, 2000.

Naik et al., "An Antiinflammatory Cum Immunomodulatory Piperidinylbenzopyranone From *Dysoxylum binectariferum*: Isolation, Structure and Total Synthesis," *Tetrahedron* 44:2081-2086, 1988.

Nakano et al., "PUMA, a Novel Proapoptotic Gene, Is Induced by p53," *Molecular Cell* 7:683-694, 2001.

Narita et al., "Bax interacts with the permeability transition pore to induce permeability transition and cytochrome c release in isolated mitochondria," *Proc. Natl. Acad. Sci. USA* 95:14681-14686, 1998.

Neuberger, "Generating high-avidity human Mabs in mice," *Nature Biotechnology* 14:826, 1996.

Noel et al., "Abstract C244: Development of the BET bromodomain inhibitor OTX015," *Proceedings of the AACR-NCI-EORTC International Conference: Molecular Targets and Cancer Therapeutics*, Oct. 19-23, 2013, Boston, MA, Philadelphia, PA: AACR; *Mol Cancer Ther* 12(11 Suppl): Abstract No. C244, 2013. (4 pages).

O'Brien et al., "Phase I to II Multicenter Study of Oblimersen Sodium, a Bcl-2 Antisense Oligonucleotide, in Patients With Advanced Chronic Lymphocytic Leukemia," *Journal of Clinical Oncology* 23(30):7697-7702, 2005.

O'Connor et al., "Bim: a novel member of the Bcl-2 family that promotes apoptosis," *The EMBO Journal* 17(2):384-395, 1998.

Oda et al., "Noxa, a BH3-Only Member of the Bcl-2 Family and Candidate Mediator of p53-Induced Apoptosis," *Science* 288:1053-1058, 2000.

Oh et al., "Conformational Changes in BID, a Pro-apoptotic BCL-2 Family Member, upon Membrane Binding," *The Journal of Biological Chemistry* 280(1):753-767, 2005.

Oltersdorf et al., "An inhibitor of Bcl-2 family proteins induces regression of solid tumours," *Nature* 435:677-681, 2005.

Opferman et al., "Development and maintenance of B and T lymphocytes requires antiapoptotic MCL-1," *Nature* 426:671-676, 2003.

Oscier et al., "Multivariate analysis of prognostic factors in CLL: clinical stage, IGVH gene mutational status, and loss or mutation of the p53 gene are independent prognostic factors," *Blood* 100:1177-1184, 2002.

Paoluzzi et al., "The BH3-only mimetic ABT-737 synergizes the antineoplastic activity of proteasome inhibitors in lymphoid malignancies," *Blood* 112:2906-2916, 2008.

Paquin et al., "Design and synthesis of 4-[(s-triazin-2-ylamino)methyl]-N-(2-aminophenyl)-benzamides and their analogues as a novel class of histone deacetylase inhibitors," *Bioorganic & Medicinal Chemistry Letters* 18:1067-1071, 2008.

Parker et al., "Early Induction of Apoptosis in Hematopoietic Cell Lines After Exposure to Flavopiridol," *Blood* 91:458-465, 1998.

Parry et al., "Dinaciclib (SCH 727965), a Novel and Potent Cyclin-Dependent Kinase Inhibitor," *Mol Cancer Ther* 9(8):2344-2353, 2010.

Paruch et al., "Discovery of Dinaciclib (SCH 727965): A Potent and Selective Inhibitor of Cyclin-Dependent Kinases,"*ACS Med. Chem. Lett* 1:204-208, 2010.

Perkins et al., "Frequency and Type of Serious Infections in Fludarabine-Refractory B-Cell Chronic Lymphocytic Leukemia and Small Lymphocytic Lymphoma," *Cancer* 94:2033-2039, 2002.

Picaud et al., "PFI-1, a Highly Selective Protein Interaction Inhibitor, Targeting BET Bromodomains," *Cancer Res* 73(11):3336-3346, 2013.

Piekarz et al., "Inhibitor of histone deacetylation, depsipeptide (FR901228), in the treatment of peripheral and cutaneous T-cell lymphoma: a case report," *Blood* 98:2865-2868, 2001.

Pierceall et al., "BH3 Profiling Discriminates Response to Cytarabine-Based Treatment of Acute Myelogenous Leukemia," *Molecular Cancer Therapeutics* 12(12):2940-2949, 2013.

Pierceall et al., "Mcl-1 Dependence Predicts Response to Vorinostat and Gemtuzumab Ozogamicin in Acute Myeloid Leukemia," *Leuk Res* 38:564-568, 2014. (13 pages).

Pierceall et al., "Mitochondrial Priming of Chronic Lymphocytic Leukemia Patients Associates Bcl-$x_L$ Dependence with Alvocidib Response," *Leukemia* 28:2251-2254, 2014. (7 pages).

Pinkert et al., "An albumin enhancer located 10 kb upstream functions along with its promoter to direct efficient, liver-specific expression in transgenic mice," *Genes & Development* 1:268-276, 1987.

Plumb et al., "Pharmacodynamic Response and Inhibition of Growth of Human Tumor Xenografts by the Novel Histone Deacetylase Inhibitor PXD101,"*Molecular Cancer Therapeutics* 2:721-728, 2003.

Pode-Shakked et al., "Development tumourigenesis: NCAM as a putative marker for the malignant renal stem/progenitor cell population," *J. Cell. Mol. Med.* 13(8B): 1792-1808, 2009.

Polster et al., "BH3 Death Domain Peptide Induces Cell Type-selective Mitochondrial Outer Membrane Permeability," *The Journal of Biological Chemistry* 276:37887-37894, 2001.

Presta, "Antibody engineering," *Current Opinion in Structural Biology* 2:593-596, 1992.

Pritzker, "Cancer Biomarkers: Easier Said Than Done," *Clinical Chemistry* 48(8):1147-1150, 2002.

(56) References Cited

OTHER PUBLICATIONS

Putcha et al., "Induction of BIM, a Proapoptotic BH3-Only BCL-2 Family Member, Is Critical for Neuronal Apoptosis," *Neuron* 29:615-628, 2001.
Puthalakath et al., "The Proapoptotic Activity of the Bcl-2 Family Member Bim is Regulated by Interaction with the Dynein Motor Complex," *Molecular Cell* 3:287-296, 1999.
Puthalakath et al., "Bmf: A Proapoptotic BH3-Only Protein Regulated by Interaction with the Myosin V Actin Motor Complex, Activated by Anoikis," *Science* 293:1829-1832, 2001.
Puthalakath et al., "Keeping killers on a tight leash: transcriptional and post-translational control of the pro-apoptotic activity of BH3-only proteins," *Cell Death and Differentiation* 9:505-512, 2002.
Quinsay et al., "Abstract 1783: Pro-Apoptotic Bnip3 Mediates Permeabilization of Mitochondria and Release of Cytochrome c via a Novel Mechanism," *Circulation* 118:S388. 2008. (5 pages).
Raff, "Social controls on cell survival and cell death," *Nature* 356:397-400, 1992.
Rassenti et al., "ZAP-70 Compared with Immunoglobulin Heavy-Chain Gene Mutation Status as a Predictor of Disease Progression in Chronic Lymphocytic Leukemia," *N. Engl. J. Med.* 351:893-901, 2004.
Ray et al., "BNIP3 Heterodimerizes with Bcl-2/Bcl-$X_L$ and Induces Cell Death Independent of a Bcl-2 Homology 3 (BH3) Domain at Both Mitochondrial and Nonmitochondrial Sites," *The Journal of Biological Chemistry* 275(2):1439-1448, 2000.
Raychaudhuri, "Low probability Bid-Bax reaction generates heterogeneity in apoptosis resistance of cancer and cancer stem cells," arXiv:1108.2091 [q-bio.MN], 2011, 17 pages.
Ren et al., "BID, BIM, and PUMA Are Essential for Activation of the BAX- and BAK-Dependent Cell Death Program," *Science* 330:1390-1393, 2010.
Rezaei et al., "Leukemia markers expression of peripheral blood vs. bone marrow blasts using flow cytometry," *Med Sci. Monit* 9:CR359-CR362, 2003.
Richon et al., "A class of hybrid polar inducers of transformed cell differentiation inhibits histone deacetylases," *Proc. Natl. Acad. Sci. USA* 95:3003-3007, 1998.
Riechmann et al., "Reshaping human antibodies for therapy," *Nature* 332:323-327, 1988.
Rollins-Raval et al., "The value of immunohistochemistry for CD14, CD123, CD33, myeloperoxidase and CD68R in the diagnosis of acute and chronic myelomonocytic leukaemias," *Histopathology* 60:933-942, 2012.
Rothbard et al., "Conjugation of arginine oligomers to cyclosporin A facilitates topical delivery and inhibition of inflammation," *Nature Medicine* 6(11):1253-1257, 2000.
Rudek et al., "Clinical Pharmacology of Flavopiridol Following a 72-Hour Continuous Infusion," *Ann Pharmacother* 37:1369-1374, 2003.
Ryan et al., "Heightened mitochondrial priming is the basis for apoptotic hypersensitivity of $CD4^+$ $CD8^+$ thymocytes," *PNAS* 107(29): 12895-12900, 2010.
Ryan et al., "BH3 Profiling in Whole Cells by Fluorimeter or FACS," *Methods* 61:156-164, 2013. (22 pages).
Saito et al., "A synthetic inhibitor of histone deacetylase, MS-27-275, with marked in vivo antitumor activity against human tumors," *Proc. Natl. Acad. Sci. USA* 96:4592-4597, 1999.
Samson et al., "A 35 Amino Acid Fragment of Leptin Inhibits Feeding in the Rat," *Endocrinology* 137(11):5182-5185, 1996.
Sattler et al., "Structure of Bcl-$x_L$-Bak Peptide Complex: Recognition Between Regulators of Apoptosis," *Science* 275:983-986, 1997.
Sausville et al., "Inhibition of CDKs as a Therapeutic Modality," *Ann. NY Acad. of Sci.* 910:207-222, 2000.
Schimmer et al., "The BH3 domain of BAD fused to the Antennapedia peptide induces apoptosis via its alpha helical structure and independent of Bcl-2," *Cell Death and Differentiation* 8:725-733, 2001.

Schwartz et al., "Phase II Study of the Cyclin-Dependent Kinase Inhibitor Flavopiridol Administered to Patients With Advanced Gastric Carcinoma," *J Clin Oncol* 19:1985-1992, 2001.
Seal et al., "Identification of a novel series of BET family bromodomain inhibitors: Binding mode and profile of I-BET151 (GSK1210151A)," *Bioorganic & Medicinal Chemistry Letters* 22:2968-2972, 2012.
Sedlacek et al., "Flavopiridol (L86 8275; NSC 649890), a new kinase inhibitor for tumor therapy," *International Journal of Oncology* 9:1143-1168, 1996.
Sen et al., "Artemisinin triggers induction of cell-cycle arrest and apoptosis in *Leishmania donovani* promastigotes," *Journal of Medical Microbiology* 56:1213-1218, 2007.
Senderowicz et al., "Phase I Trial of Continuous Infusion Flavopiridol, a Novel Cyclin-Dependent Kinase Inhibitor, in Patients With Refractory Neoplasms," *J. Clin Oncol* 16:2986-2999, 1998.
Senderowicz et al., "Preclinical and Clinical Development of Cyclin-Dependent Kinase Modulators," *J Natl Cancer Inst* 92:376-387, 2000.
Shalaby et al., "Development of Humanized Bispecific Antibodies Reactive with Cytotoxic Lymphocytes and Tumor Cells Overexpressing the HER2 Protooncogene," *J. Exp. Med.* 175:217-225, 1992.
Shangary et al., "Peptides Derived from BH3 Domains of Bcl-2 Family Members: A Comparative Analysis of Inhibition of Bcl-2, Bcl-$x_L$ and Bax Oligomerization, Induction of Cytochrome c Release, and Activation of Cell Death," *Biochemistry* 41:9485-9495, 2002.
Shapiro et al., "A Phase II Trial of the Cyclin-dependent Kinase Inhibitor Flavopiridol in Patients with Previously Untreated Stage IV Non-Small Cell Lung Cancer," *Clinical Cancer Research* 7:1590-1599, 2001.
Shibue et al., "Differential contribution of Puma and Noxa in dual regulation of p53-mediated apoptotic pathways," *The EMBO Journal* 25:4952-4962, 2006.
Shimizu et al., "Proapoptotic BH3-only Bcl-2 family members induce cytochrome c release, but not mitochondrial membrane potential loss, and do not directly modulate voltage-dependent anion channel activity," *PNAS* 97:577-582, 2000.
Shopes, "A Genetically Engineered Human IgG Mutant With Enhanced Cytolytic Activity," *The Journal of Immunology* 148(9):2918-2922, 1992.
Sinicrope et al., "Proapoptotic Bad and Bid Protein Expression Predict Survival in Stages II and III Colon Cancers," *Clin Cancer Res* 14(13):4128-4133, 2008.
Sinicrope et al., "Prognostic Impact of Bim, Puma, and Noxa Expression in Human Colon Carcinomas," *Clin Cancer Res* 14(18):5810-5818, 2008.
Smith et al., "Enhancer biology and enhanceropathies," *Nature Structural & Molecular Biology* 21:210-219, 2014.
Smith et al., "An alvocidib-containing regimen is highly effective in AML patients through a mechanism dependent on MCL1 expression and function," *2015 ASCO Annual Meeting*, Abstract No. 7062, 2015. (3 pages).
Soltow et al., "Overexpression of CuZnSOD or MnSOD protects satellite cells from doxorubicin-induced apoptosis," *The FASEB Journal* 21(5): Abstract No. A449, 2007. (2 pages).
Song et al., "Carbon Monoxide Promotes Fas/CD95-induced Apoptosis in Jurkat Cells," *The Journal of Biological Chemistry* 279(43):44327-44334, 2004. (11 pages).
Song et al., "Carbon Monoxide Promotes Fas/CD95-induced Apoptosis in Jurkat Cells," *The Journal of Biological Chemistry* 279(43):44327-44334, 2004—"Additions and Correction," *The Journal of Biological Chemistry* 280(23):22555-22556, 2005. (3 pages).
Stevenson et al., "A chimeric antibody with dual Fc regions (bisFabFc) prepared by manipulations at the IgG hinge," *Anti-Cancer Drug Design* 3:219-230, 1989.
Stewart et al., "The MCL-1 BH3 Helix is an Exclusive MCL-1 inhibitor and Apoptosis Sensitizer," *Nat. Chem. Biol.* 6(8):595-601, 2010. (17 pages).
Sturm et al., "Mutation of p53 and consecutive selective drug resistance in B-CLL occurs as a consequence of prior DNA-damaging chemotherapy," *Cell Death and Differentiation* 10:477-484, 2003.

(56) References Cited

OTHER PUBLICATIONS

Sugiyama et al., "Activation of mitochondiial voltage-dependent anion channel by a pro-apoptotic BH3-only protein Bim," *Oncogene* 21:4944-4956, 2002.
Suzuki et al., "Possible Existence of Common Internalization Mechanisms among Arginine-rich Peptides," *The Journal of Biological Chemistry* 277(4):2437-2443, 2002.
Tahir et al., "Potential mechanisms of resistance to venetoclax and strategies to circumvent it," *BMC Cancer* 17:399, 2017. (10 pages).
Tan et al., "Phase I Clinical and Pharmacokinetic Study of Flavopiridol Administered as a Daily 1-Hour Infusion in Patients With Advanced Neoplasms," *J Clin Oncol* 20:4074-4082, 2002.
Taussig et al., "Anti-CD38 antibody-mediated clearance of human repopulating cells masks the heterogeneity of leukemia-initiating cells," *Blood* 112:568-575, 2008.
Terradillos et al., "Direct addition of BimL to mitochondria does not lead to cytochrome c release," *FEBS Letters* 522:29-34, 2002.
Theisen et al., "Reversible inhibition of lysine specific demethylase 1 is a novel anti-tumor strategy for poorly differentiated endometrial carcinoma," *BMC Cancer* 14:752, 2014. (12 pages).
Thomas et al., "Phase I clinical pharmacokinetic trial of the cyclin-dependent kinase inhibitor flavopiridol," *Cancer Chemother Pharmacol* 50:465-472, 2002.
Thomenius et al., "Using BH3 Profiling As a Predictive Indicator for Myeloma Patient Response to Bortezomib," *Blood* 118:3952, 2011. (6 pages).
Thornton et al., "High dose methyl prednisolone can induce remissions in CLL patients with p53 abnormalities," *Ann Hematol* 82:759-765, 2003.
Thornton et al., "Characterisation of TP53 abnormalities in chronic lymphocytic leukaemia," *The Hematology Journal* 5:47-54, 2004.
Tolero Pharmaceuticals, "Jefferies 2016 Heathcare Conference," 2016, 31 pages.
Toogood et al., "Discovery of a Potent and Selective Inhibitor of Cyclin-Dependent Kinase 4/6," *J. Med. Chem.* 48:2388-2406, 2005.
Touzeau et al., "BH3-profiling identifies heterogeneous dependency of Bcl-2 family members in Multiple Myeloma and predicts sensitivity to BH3 mimetics," *Leukemia* 30(3):761-764, 2016. (8 pages).
Traunecker et al., "Bispecific single chain molecular (Janusins) target cytotoxic lymphocytes on HIV infected cells," *The EMBO Journal* 10(12):3655-3659, 1991.
Tsao et al., "Concomitant inhibition of DNA methyltransferase and BCL-2 protein function synergistically induce mitochondrial apoptosis in acute myelogenous leukemia cells," *Ann Hemaltol* 91(12):1861-1870, 2012.
Tutt et al., "Trispecific F(ab')$_3$ Derivatives That Use Cooperative Signaling Via the TCR/CD3 Complex and CD2 to Activate and Redirect Resting Cytotoxic T Cells," *The Journal of Immunology* 147(1):60-69, 1991.
Valencia et al., "A new reliable fluorescence in situ hybridization method for identifying multiple specific cytogenetic abnormalities in acute myeloid leukemia," *Leukemia & Lymphoma* 51(4):680-685, 2010.
Vaquero et al., "Extracellular Matrix Proteins Protect Pancreatic Cancer Cells From Death Via Mitochondrial and Nonmitochondrial Pathways," *Gastroenterology* 125:1188-1202, 2003.
Vaux et al., "Bcl-2 gene promotes haemopoietic cell survival and cooperates with c-myc to immortalize pre-B cells," *Nature* 335:440-442, 1988.
Venkat, "Flavopiridol: A Drug that May Save Lives," 2004, retrieved from https://web.archive.org/web/20060615112217/http://clltopics.org/Chemo/flavopiridol.htm, 7 pages.
Venugopal et al., "A Phase I Study of Quisinostat (JNJ-26481585), an Oral Hydroxamate Histone Deacetylase Inhibitor with Evidence of Target Modulation and Antitumor Activity, in Patients with Advanced Solid Tumors," *Clin Cancer Res* 19(15):4262-4272, 2013.
Verhoeyen et al., "Reshaping Human Antibodies: Grafting an Antilysozyme Activity," *Science* 239:1534-1536, 1988.
Ververis et al., "Histone deacetylase inhibitors (HDACIs): multitargeted anticancer agents," *Biologics: Targets and Therapy* 7:47-60, 2013.
Vitetta et al., "Redesigning Nature's Poisons to Create Anti-Tumor Reagents," *Science* 238:1098-1104, 1987.
Vivès et al., "A Truncated HIV-1 Tat Protein Basic Domain Rapidly Translocates through the Plasma Membrane and Accumulates in the Cell Nucleus," *The Journal of Biological Chemistry* 272(25):16010-16017, 1997.
Vo, "Mitochondrial Priming Determines Chemotherapeutic Response in Acute Myeloid Leukemia," Dissertation, The Division of Medical Sciences, Harvard University, Cambridge, Massachusetts, Apr. 2012, 119 pages.
Vo et al., "Relative Mitochondrial Priming of Myeloblasts and Normal HSCs Determines Chemotherapeutic Success in AML," *Cell* 151:344-355, 2012.
Wang, "The expanding role of mitochondria in apoptosis," *Genes & Development* 15:2922-2933, 2001.
Wang et al., "BID: a novel BH3 domain-only death agonist," *Genes & Development* 10:2859-2869, 1996.
Wang et al., "Cell Permeable Bcl-2 Binding Peptides: A Chemical Approach to Apoptosis Induction in Tumor Cells," *Cancer Research* 60:1498-1502, 2000.
Wang et al., "Structure-based discovery of an organic compound that binds Bcl-2 protein and induces apoptosis of tumor cells," *PNAS* 97(13):7124-7129, 2000.
Wei et al., "tBID, a membrane-targeted death ligand, oligomerizes BAK to release cytochrome c," *Genes & Development* 14:2060-2071, 2000.
Wei et al., "Proapoptotic BAX and BAK: A Requisite Gateway to Mitochondrial Dysfunction and Death," *Science* 292:727-730, 2001.
Weinstein, "Addiction to Oncogenes—the Achilles Heal of Cancer," *Science* 297:63-64, 2002.
Weniger et al., "Treatment-Induced Oxidative Stress and Cellular Antioxidant Capacity Determine Response to Bortezomib in Mantle Cell Lymphoma," *Clinical Cancer Research* 17(15):5101-5112, 2011.
Werner et al., "Bcl-2 Family Member Bfl-1/A1 Sequesters Truncated Bid to Inhibit Its Collaboration with Pro-apoptotic Bak or Bax," *The Journal of Biological Chemistry* 277(25):22781-22788, 2002.
Westerhoff et al., "Magainins and the disruption of membrane-linked free-energy transduction," *Proc. Natl. Acad. Sci. USA* 86:6597-6601, 1989.
Wilkinson, "Ultimate Abs—Immunochemical techniques inspire development of new antibody purification methods," *The Scientist* 14(8):25-28, 2000. (6 pages).
Willis et al., "Proapoptotic Bak is sequestered by Mcl-1 and Bcl-$x_L$, but not Bcl-2, until displaced by BH3-only proteins," *Genes & Development* 19:1294-1305, 2005.
Willis et al., "Apoptosis Initiated When BH3 Ligands Engage Multiple Bcl-2 Homologs, Not Bax or Bak," *Science* 315:856-859, 2007.
Wolff et al., "Monoclonal Antibody Homodimers: Enhanced Antitumor Activity in Nude Mice," *Cancer Research* 53:2560-2565, 1993.
Wolter et al., "Movement of Bax from the Cytosol to Mitochondria during Apoptosis," *The Journal of Cell Biology* 139(5):1281-1292, 1997.
Worland et al., "Alteration of the Phosphorylation State of p34$^{cdc2}$ Kinase by the Flavone L86-8275 in Breast Carcinoma Cells," *Biochemical Pharmacology* 46(10):1831-1840, 1993.
Woyach et al., "Targeted therapies in CLL: mechanisms of resistance and strategies for management," *Blood* 126:471-477, 2015.
Wyatt et al., "Identification of N-(4-Piperidinyl)-4-(2,6-dichlorobenzoylamino)-1H-pyrazole-3-carboxamide (AT7519), a Novel Cyclin Dependent Kinase Inhibitor Using Fragment-Based X-Ray Crystallography and Structure Based Drug Design," *J. Med. Chem.* 51:4986-4999, 2008.
Yamaguchi et al., "Bcl-XL Protects BimEL-induced Bax Conformational Change and Cytochrome c Release Independent of Interacting with Bax or BimEL," *The Journal of Biological Chemistry* 277(44):41604-41612, 2002.

(56) References Cited

OTHER PUBLICATIONS

Yang et al., "[11] Calculation of Protein Conformation from Circular Dichroism," *Methods Enzymol* 130:208-269, 1986.
Yang et al., "Bad, a Heterodimeric Partner for Bcl-$x_L$ and Bcl-2, Displaces Bax and Promotes Cell Death," *Cell* 80:285-291, 1995.
Yang et al., "A novel liposomal formulation of flavopiridol," *International Journal of Pharmaceutics* 365:170-174, 2009.
Yang et al., "Bone marrow stroma-mediated resistance to FLT3 inhibitors in FLT3-ITD AML is mediated by persistent activation of extracellular regulated kinase," *British Journal of Haematology* 164:61-72, 2014.
Yasuda et al., "BNIP3α: A Human Homolog of Mitochondrial Proapoptotic Protein BNIP3," *Cancer Research* 59:533-537, 1999.
Yeh et al., "Up-regulation of CDK9 kinase activity and Mcl-1 stability contributes to the acquired resistance to cyclin-dependent kinase inhibitors in leukemia," *Oncotarget* 6(5):2667-2679, 2014.
Yi et al., "Inhibition of Bid-induced Apoptosis by Bcl-2," *The Journal of Biological Chemistry* 278(19):16992-16999, 2003.
Yu et al., "Catalytic site remodelling of the DOT1L methyltransferase by selective inhibitors," *Nature Communications* 3:1288, 2012. (12 pages).
Zeng et al., "Targeting the leukemia microenvironment by CXCR4 inhibition overcomes resistance to kinase inhibitors and chemotherapy in AML," *Blood* 113:6215-6224, 2009.
Zha et al., "Serine Phosphorylation of Death Agonist BAD in Response to Survival Factor Results in Binding to 14-3-3 Not BCL-$X_L$," *Cell* 87:619-628, 1996.
Zha et al., "BH3 Domain of BAD Is Required for Heterodimerization with BCL-$X_L$ and Pro-apoptotic Activity," *The Journal of Biological Chemistry* 272(39):24101-24104, 1997.
Zha et al., "Posttranslational N-Myristoylation of BID as a Molecular Switch for Targeting Mitochondria and Apoptosis," *Science* 290:1761-1765, 2000.
Zhai et al., "Clinical pharmacology and pharmacogenetics of flavopiridol 1-h i.v. infusion in patients with refractory neoplasms," *Anti-Cancer Drugs* 14:125-135, 2003.
Zhao et al., "The Making of I-BET762, a BET Bromodomain Inhibitor Now in Clinical Development," *J. Med. Chem.* 56:7498-7500, 2013.
Zhou et al., "Novel mutant-selective EGFR kinase inhibitors against EGFR T790M," *Nature* 462(7276):1070-1074, 2009.
Zong et al., "BH3-only proteins that bind pro-survival Bcl-2 family members fail to induce apoptosis in the absence of Bax and Bak," *Genes & Development* 15:1481-1486, 2001.
Harada et al., "Discovery of potent and orally bioavailable 17β-hydroxysteroid dehydrogenase type 3 inhibitors," *Bioorganic & Medicinal Chemistry* 20 :3242-3254, 2012.
Okamoto et al., "Increased antitumor potential of the raloxifene prodrug, raloxifene diphosphate," *Int. J. Cancer* 122 :2142-2147, 2008.
Wang et al., "Synthesis of pochoxime prodrugs as potent HSP90 inhibitors," *Bioorganic & Medicinal Chemistry Letters* 19:3836-3840, 2009.

\* cited by examiner

ALVOCIDIB PRODRUGS HAVING INCREASED BIOAVAILABILITY

BACKGROUND

Technical Field

The present invention is generally directed to phosphate prodrugs of alvocidib and use of the same for treatment of cancer.

Description of the Related Art

Cyclin-dependent kinases (CDKs) are important regulators that control the timing and coordination of the cell cycle. CDKs form reversible complexes with their obligate cyclin partners to control transition through key junctures in the cell cycle. For example, the activated CDK4-cyclin D1 complex controls progression through the G1 phase of the cell cycle, while the CDK1-cyclin B1 complex controls entry into the mitotic phase of the cell cycle. Endogenous cyclin dependent kinase inhibitory proteins (CDKIs) are known to bind either the CDK or cyclin component and inhibit the kinase activity of the complex. In many tumors such as melanomas, pancreatic and esophageal cancers, these natural CDKIs are either absent or mutated. Thus, selective CDK inhibitors may prove to be effective chemotherapeutic agents.

Alvocidib (also known as Flavopiridol) is a synthetic flavone having the following structure:

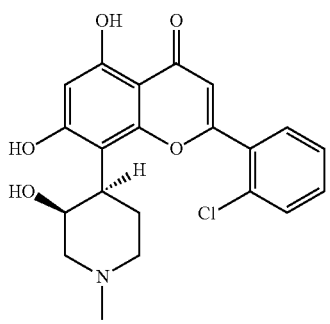

Alvocidib is a potent and selective inhibitor of the CDKs and has antitumor activity against various tumor cells lines, such as human lung carcinoma and breast carcinoma and also inhibits tumor growth in xenograft models. Alvocidib has been shown to induce arrest in both the G1 and G2 phases of the cell cycle and also inhibit polymerase II driven transcription by inhibiting CDK9. By inhibiting CDK9, which forms part of the complex known as the positive transcription elongation factor or P-TEFb, alvocidib treatment reduces the expression of key oncogenes such MYC and key anti-apoptotic proteins such as MCL1. Accordingly, alvocidib is an attractive therapeutic agent for cancer and is currently undergoing clinical trials in relapsed/refractory AML patients.

Oral administration of alvocidib has been limited by gastrointestinal toxicity and limited oral bioavailability. Further, preclinical studies suggest that prolonged exposure may be important for maximizing alvocidib's activity. Accordingly, continuous intravenous infusion schedules have been extensively explored in human trials. Alternative hybrid dosing, including an intravenous bolus dose followed by a slow infusion have also been explored, but to date there have been no reports of orally delivering a therapeutically effective amount of alvocidib.

While progress has been made, there remains a need in the art for increasing the oral bioavailability of alvocidib. The present invention fulfills this need and provides related advantages.

BRIEF SUMMARY

In brief, embodiments of the present invention provide phosphate prodrugs of alvocidib having increased bioavailability relative to the alvocidib parent compound. Accordingly, in one embodiment is provided a compound having the following structure (I):

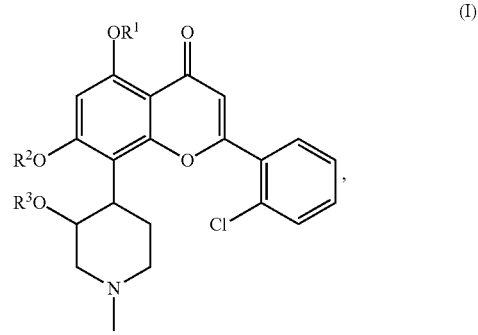

or a stereoisomer, tautomer or pharmaceutically acceptable salt thereof, wherein:

one of $R^1$, $R^2$ or $R^3$ is $-P(=O)(OH)_2$, and the other two of $R^1$, $R^2$ and $R^3$ are each H.

Other embodiments are directed to a pharmaceutical composition comprising a pharmaceutically acceptable carrier or excipient and a compound of structure (I). Methods for use of the compound of structure (I), and pharmaceutical compositions comprising the same, for treatment of a disease associated with overexpression of a cyclin-dependent kinase (CDK) in a mammal in need thereof are also provided.

These and other aspects of the invention will be apparent upon reference to the following detailed description. To this end, various references are set forth herein which describe in more detail certain background information, procedures, compounds and/or compositions, and are each hereby incorporated by reference in their entirety.

DETAILED DESCRIPTION

Figure 1:
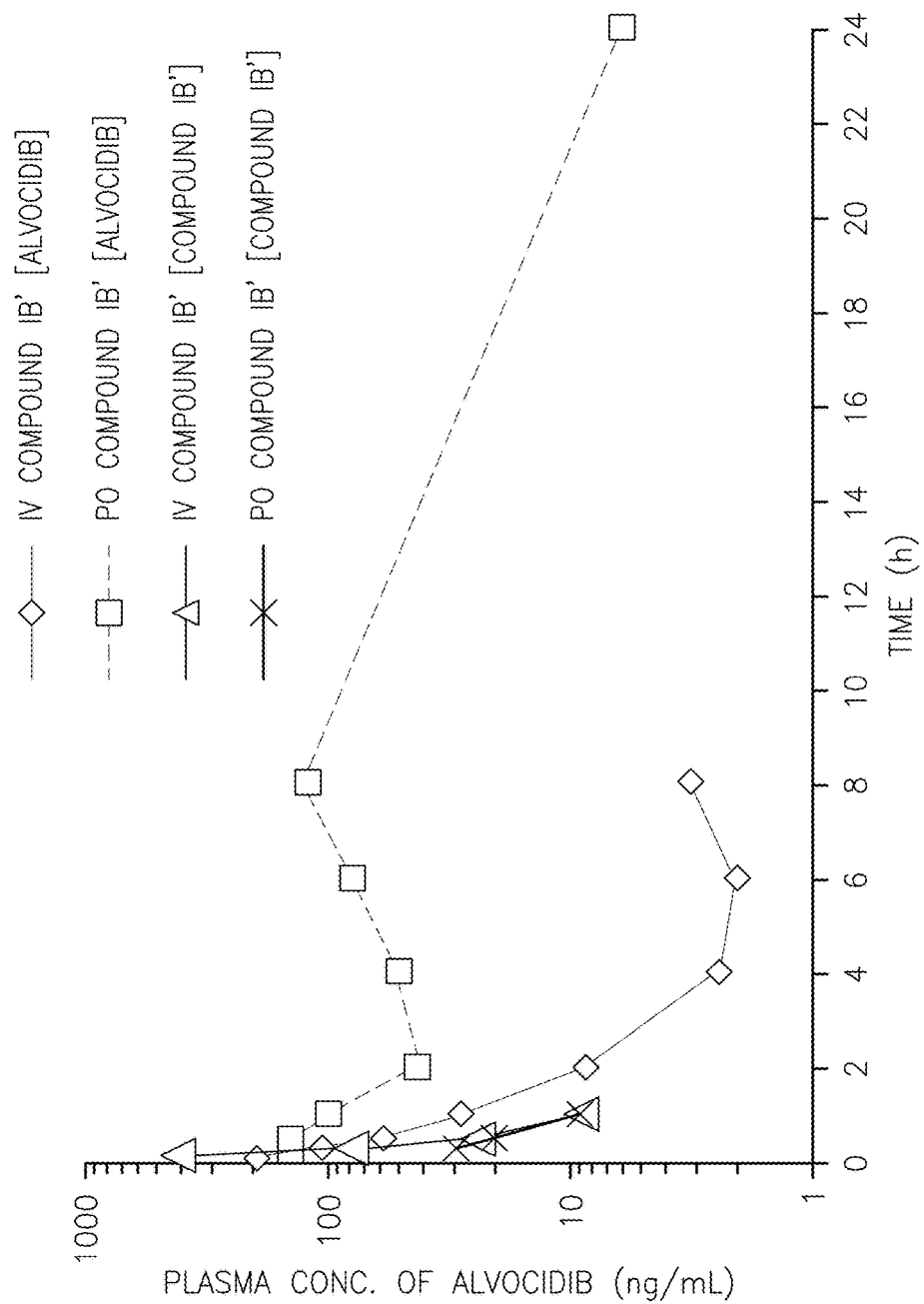
FIG. 1 shows the pharmacokinetic profile of alvocidib and compound IB following the administration of compound IB to Sprague Dawley rats.

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

Embodiments of the present invention include phosphate prodrugs of alvocidib. "Phosphate" refers to the —OP(=O)(OH)$_2$ moiety. For ease of illustration the phosphate moieties herein are often depicted in the di-protonated form, but also exist in the mono-protonated (—OP(=O)(OH)(O$^-$)) and unprotonated forms (—OP(=O)(O$^-$)$_2$), depending on pH. The mono- and unprotonated forms will typically be associated with a counterion, such that the compounds are in the form of a pharmaceutically acceptable salt. Such mono- and unprotonated forms, and their pharmaceutically acceptable salts, are encompassed within the scope of the inventions, even if not specifically illustrated in the chemical structures.

"Prodrug" is meant to indicate a compound that may be converted under physiological conditions or by solvolysis to a biologically active compound described herein (e.g., compound of structure (I)). Thus, the term "prodrug" refers to a precursor of a biologically active compound that is pharmaceutically acceptable. In some aspects, a prodrug is inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

A "compound of the invention" refers to a compound of structure (I), and its substructures, as defined herein.

Embodiments of the invention disclosed herein are also meant to encompass all pharmaceutically acceptable compounds of structure (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabelled compounds could be useful to help determine or measure the effectiveness of the compounds, by characterizing, for example, the site or mode of action, or binding affinity to pharmacologically important site of action. Certain isotopically-labelled compounds of structure (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of structure (I) can generally be prepared by conventional techniques known to those skilled in the art or by processes analogous to those described in the Preparations and Examples as set out below using an appropriate isotopically-labeled reagent in place of the non-labeled reagent previously employed.

Embodiments of the invention disclosed herein are also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, embodiments of the invention include compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, embodiments of the compounds of the present invention may exist as a hydrate, including a monohydrate, dihydrate, hemihydrate, sesquihydrate, trihydrate, tetrahydrate and the like, as well as the corresponding solvated forms. Embodiments of the compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Mammal" includes humans and both domestic animals such as laboratory animals and household pets (e.g., cats, dogs, swine, cattle, sheep, goats, horses, rabbits), and non-domestic animals such as wildlife and the like.

"Effective amount" or "therapeutically effective amount" refers to that amount of a compound of the invention which, when administered to a mammal, preferably a human, is sufficient to effect treatment, as defined below, of a disease associated with overexpression of a cyclin-dependent kinase (CDK) in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. Embodiments of the present invention contemplate various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. Embodiments of the present invention include tautomers of any said compounds.

I. Compounds

As noted above, embodiments of the present disclosure are directed to prodrugs of alvocidib having increased bioavailability relative to the parent compound. Surprisingly, experiments performed in support of the present invention demonstrate that a monophosphate analogue of alvocidib has a bioavailability of approximately 1.3 times the parent alvocidib compound when delivered orally to CD-1 mice and more than 8 times that of the related diphosphate prodrugs. The presently disclosed monophosphate compounds are metabolized to alvocidib in vivo and, while not wishing to be bound by theory, it is believed that the increase in bioavailability of alvocidib released from the monophosphate prodrug compared to the alvocidib parent compound is related to a slower rate of metabolism of the prodrug compared to alvocidib. Other expected advantages of the present compounds include increased solubility in typical pharmaceutical formulations, in water and in bodily fluids, and decreased toxicity relative to the alvocidib parent compound when administered orally.

Accordingly, in one embodiment a compound is provided having the following structure (I):

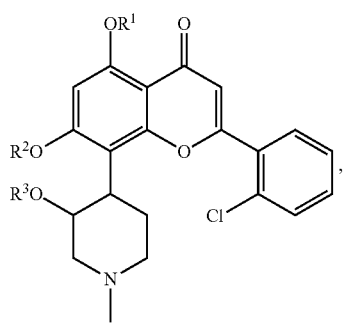

or a stereoisomer, tautomer or pharmaceutically acceptable salt thereof, wherein:

one of $R^1$, $R^2$ or $R^3$ is —P(=O)(OH)$_2$, and the other two of $R^1$, $R^2$ and $R^3$ are each H.

In certain embodiments, the compound has the following structure (I'):

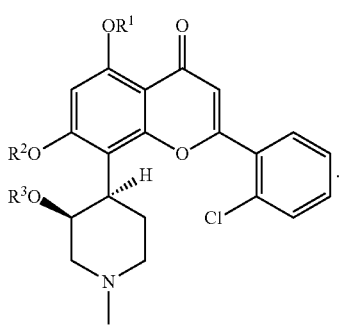

In some other embodiments, the compound has the following structure (IA):

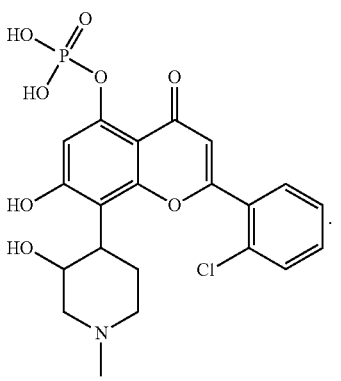

In some more embodiments, the compound has the following structure (IA'):

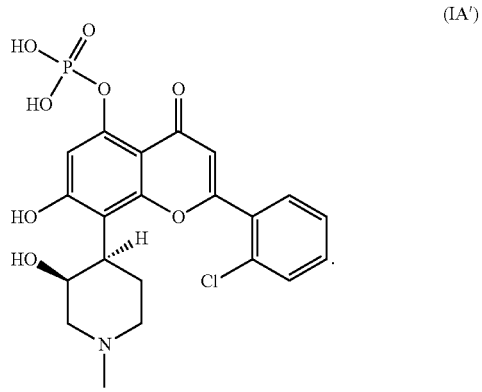 [SMILES: CN1CC[C@H](c2c(O)cc(OP(=O)(O)O)c3c(=O)cc(-c4ccccc4Cl)oc23)[C@H](O)C1]

In yet other embodiments, the compound has the following structure (IB):

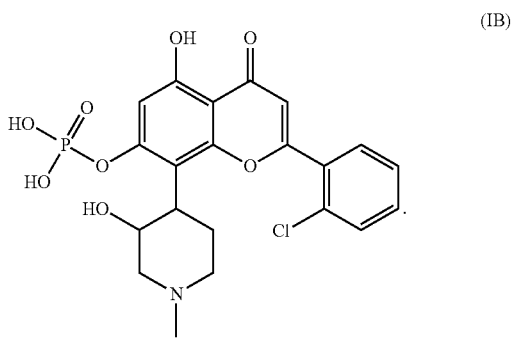 [SMILES: CN1CCC(c2c(OP(=O)(O)O)cc(O)c3c(=O)cc(-c4ccccc4Cl)oc23)C(O)C1]

In other different embodiments, the compound has the following structure (IB'):

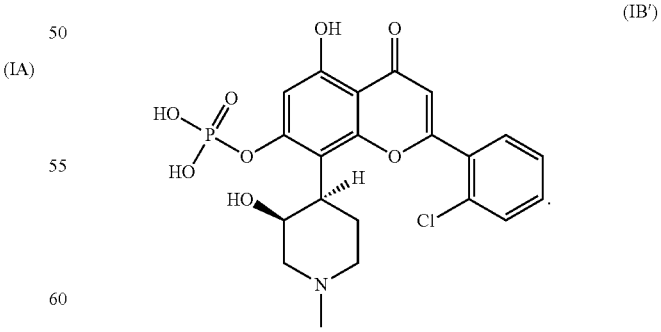

In still more embodiments, the compound has the following structure (IC):

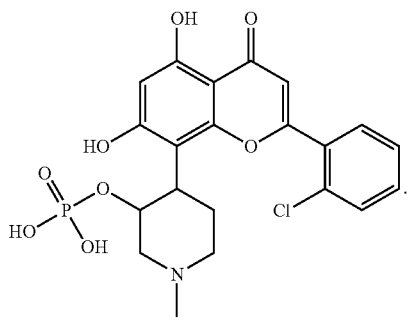

(IC)

In some other different embodiments, the compound has the following structure (IC'):

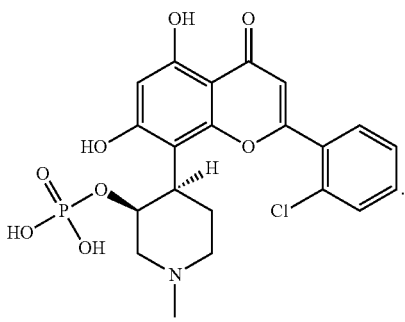

(IC')

In some embodiments, any of the foregoing compounds are in the form of a pharmaceutically acceptable salt. The salt may be an acid addition salt or a base addition salt. For example, the salt may be an amine salt formed by protonation of the N-methyl piperazine moiety (e.g., HCl salt and the like). In other embodiments, the salt is formed at the phosphate, and the compounds are in the form of mono- or di-salts of the phosphate group (e.g., mono- or disodium phosphate salt and the like). All pharmaceutically acceptable salts of the foregoing compounds are included in the scope of the invention.

Also provided are pharmaceutical compositions comprising a pharmaceutically acceptable carrier or excipient and any of the foregoing compounds (i.e., a compound of structure (I), (I'), (IA), (IA'), (IB), (IB'), (IC) or (IC')). Advantageously, the presently disclosed compounds have increased bioavailability relative to the alvocidib parent compound, and thus certain embodiments are directed to the foregoing pharmaceutical compositions formulated for oral delivery. Any of the carriers and/or excipients known in the art for oral formulation may be used in these embodiments, in addition to other carriers and/or excipients derivable by one of ordinary skill in the art.

For the purposes of administration, the compounds of the present invention may be administered as a raw chemical or may be formulated as pharmaceutical compositions. Embodiments of the pharmaceutical compositions of the present invention comprise a compound of structure (I) and a pharmaceutically acceptable carrier, diluent or excipient. The compound of structure (I) is present in the composition in an amount which is effective to treat a particular disease or condition of interest—that is, typically in an amount sufficient to treat a disease associated with overexpression of a cyclin-dependent kinase (CDK), and preferably with acceptable toxicity to the patient. Bioavailability of compounds of structure (I) can be determined by one skilled in the art, for example, as described in the Examples below. Appropriate concentrations and dosages can be readily determined by one skilled in the art.

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of embodiments of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of some embodiments of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of some embodiments of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of certain embodiments of the invention intended for either parenteral or oral administration should contain an amount of a compound of the invention such that a suitable dosage will be obtained.

In some embodiments, the pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition of various embodiments of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

Embodiments of the pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of some embodiments of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of other embodiments of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

In some embodiments, the pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

Compounds of the invention, or pharmaceutically acceptable derivatives thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

In some embodiments, the concentration of the compound of structure (I) provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of the compound of structure (I) provided in the pharmaceutical compositions of the present invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of the compound of structure (I) provided in the pharmaceutical compositions of the present invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of the compound of structure (I) provided in the pharmaceutical compositions of the present invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount the compound of structure (I) provided in the pharmaceutical compositions of the present invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the compound of structure (I) provided in the pharmaceutical compositions of the present invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of the compound of structure (I) provided in the pharmaceutical compositions of the present invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

It will also be appreciated by those skilled in the art that, in the processes for preparing compounds of structure (I) described herein, the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

Furthermore, all compounds of the invention which exist in free base or acid form can be converted to their pharmaceutically acceptable salts by treatment with the appropriate inorganic or organic base or acid by methods known to one skilled in the art. Salts of the compounds of the invention can be converted to their free base or acid form by standard techniques.

Compounds of structure (I) can be prepared by addition of a phosphate group to one of the three free hydroxyls of alvocidib. The alvocidib parent compound (and salts and solvates thereof) can be purchased from commercial sources or prepared according to methods known in the art, for example as described in U.S. Pat. Nos. 6,136,981; 6,225,473; 6,406,912; 6,576,647; and 6,821,990; the full disclosures of which are herein incorporated by reference in their entireties.

The following General Reaction Scheme illustrates a method of making compounds of this invention, i.e., compound of structure (I):

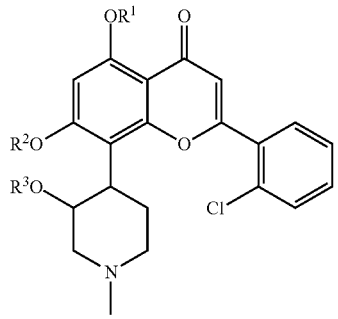

(I)

or a stereoisomer, tautomer or pharmaceutically acceptable salt thereof, wherein $R^1$, $R^2$ and $R^3$ are as defined above. It is understood that one skilled in the art may be able to make these compounds by similar methods or by combining other methods known to one skilled in the art. It is also understood that one skilled in the art would be able to make, in a similar manner as described below, other compounds of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

General Reaction Scheme 1

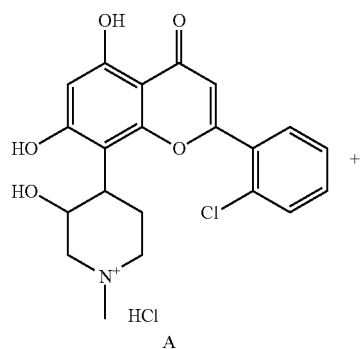

A

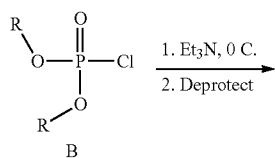

B

1. Et₃N, 0 C.
2. Deprotect

-continued

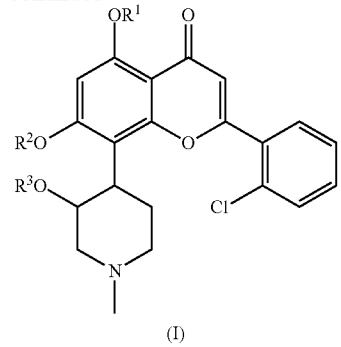

(I)

As shown in General Reaction Scheme 1, alvocidib HCl salt A is first reacted with an appropriately protected chlorophosphate (i.e., B, wherein R is a protecting group, such as ethyl). Deprotection then provides the desired compound of structure (I). It will be apparent to one of ordinary skill in the art that compounds of structure (I) having a single phosphate at any one of the three hydroxyl groups of alvocidib can be prepared according to the above scheme, and the desired regioisomer separated by usual techniques, such as chromatography. Protecting group strategies for optimizing the yield of the desired regioisomer will also be apparent to one of ordinary skill in the art.

Methods

In various embodiments, the invention provides a method for treating a disease in a mammal in need thereof by administration of a compound of structure (I), or a pharmaceutical composition comprising the same, to the mammal. In some specific embodiments, the method is for treating a disease associated with overexpression of a cyclin-dependent kinase (CDK) in a mammal in need thereof, the method comprising administering a therapeutically effective amount of any of the foregoing compounds of structure (I), or a pharmaceutical composition comprising the same, to the mammal.

In some more embodiments, the disease is cancer, for example a hematologic cancer. In some of these embodiments, the hematologic cancer is selected from acute myelogenous leukemia (AML), multiple myeloma, follicular lymphoma, acute lymphoblastic leukemia (ALL), chronic lymphocytic leukemia (CLL) and non-Hodgkin's lymphoma. In other embodiments, the hematological cancer is acute myelogenous leukemia (AML). In other different embodiments, the hematologic cancer is chronic lymphocytic leukemia (CLL). In still more different embodiments, the hematologic cancer is myelodysplasic syndrome (MDS).

In some other specific embodiments of the foregoing methods, the method comprises orally administering the compound of structure (I), or the pharmaceutical composition comprising the same, to the mammal.

In addition to the above exemplary diseases, a wide variety of cancers, including solid tumors and leukemias (e.g., acute myeloid leukemia) are amenable to the methods disclosed herein. Types of cancer that may be treated in various embodiments include, but are not limited to: adenocarcinoma of the breast, prostate, and colon; all forms of bronchogenic carcinoma of the lung; myeloid; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell). Additional types of cancers that may be treated include: histiocytic disorders; leukemia; histiocytosis malignant; Hodgkin's disease; immunoproliferative small; non-Hodgkin's lymphoma; plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor. Further, the following types of cancers are also contemplated as amenable to treatment: adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin. The types of cancers that may be treated also include, but are not limited to, angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

The compounds of the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that are used in some embodiments. An exemplary dosage is 10 to 30 mg per day. The exact dosage will depend upon the route of administration, the form in which the compound is administered, the subject to be treated, the body weight of the subject to be treated, and the preference and experience of the attending physician.

In some embodiments, a compound of the invention is administered in a single dose. A single dose of a compound of the invention may also be used for treatment of an acute condition.

In some embodiments, a compound of the invention is administered in multiple doses. In some embodiments, dosing is about once, twice, three times, four times, five times, six times, or more than six times per day. In other embodiments, dosing is about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the compounds of the invention may continue as long as necessary. In some embodiments, a compound of the invention is administered for more than 1, 2, 3, 4, 5, 6, 7, 14, or 28 days. In some embodiments, a compound of the invention is administered for less than 28, 14, 7, 6, 5, 4, 3, 2, or 1 day. In some embodiments, a compound of the invention is administered chronically on an ongoing basis, e.g., for the treatment of chronic effects.

In some embodiments, the compounds of the invention are administered in dosages. Due to intersubject variability in compound pharmacokinetics, individualization of dosing regimen is provided in certain embodiments. Dosing for a compound of the invention may be found by routine experimentation in light of the instant disclosure and/or can be derived by one of ordinary skill in the art.

EXAMPLES

Example 1

Preparation of Representative Phosphate Prodrug (IB')

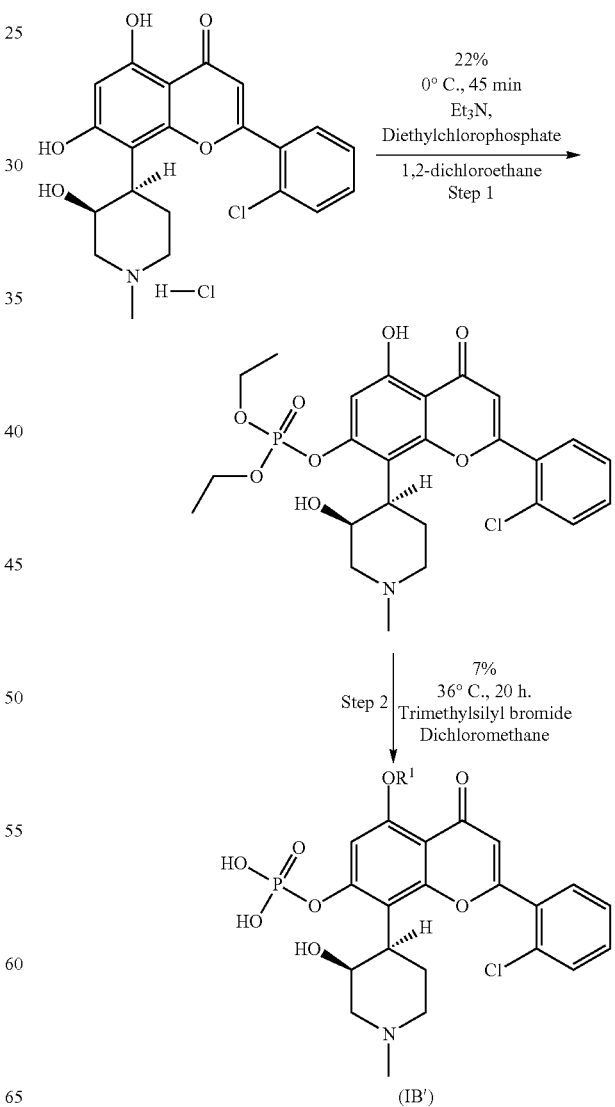

2-(2-chlorophenyl)-5-hydroxy-8-(3-hydroxy-1-methylpiperidin-4-yl)-4-oxo-4H-chromen-7-yl diethyl phosphate A suspension of alvocidib HCl (2 g, 4.56 mmol, 1 eq.) in 1,2-dichloroethane (40 mL) was cooled to 0° C. To this solution, triethylamine (1.9 mL, 13.7 mmol, 3 eq.) followed by diethylchlorophosphate (0.78 g, 4.56 mmol, 1 eq.) were added. The reaction mixture was stirred at 0° C. for 30-45 min. The reaction mixture was then poured onto ice and extracted with dichloromethane (3×25 mL). The combined organic layers were dried over anhydrous $Na_2SO_4$ and concentrated to get a crude residue. The crude residue was purified by flash column chromatography using 10-15% methanol in dichloromethane to afford 2-(2-chlorophenyl)-5-hydroxy-8-(3-hydroxy-1-methylpiperidin-4-yl)-4-oxo-4H-chromen-7-yl diethyl phosphate (550 mg, 1.02 mmol; 22%).

LCMS: Column: XBridge C8 (50×4.6 mm×3.5 μm); Mobile phase: A: 10 mM $NH_4CO_3$ in $H_2O$; B: ACN; RT: 5.97; Purity: (Max: 67.63); M+H: 538.0.

2-(2-chlorophenyl)-5-hydroxy-8-(3-hydroxy-1-methylpiperidin-4-yl)-4-oxo-4H-chromen-7-yl dihydrogen phosphate (IB')

To a solution of 2-(2-chlorophenyl)-5-hydroxy-8-(3-hydroxy-1-methylpiperidin-4-yl)-4-oxo-4H-chromen-7-yl diethyl phosphate (0.55 g, 1.02 mmol, 1 eq.) in dichloromethane (4 mL) at 0° C., trimethylsilylbromide (2.0 mL, 15.1 mmol, 15 eq.) was added. The reaction mixture was then heated at 36° C. under sealed condition for 20 h. The reaction mixture was evaporated. The crude residue obtained was purified by preparative HPLC to afford 2-(2-chlorophenyl)-5-hydroxy-8-(3-hydroxy-1-methylpiperidin-4-yl)-4-oxo-4H-chromen-7-yl dihydrogen phosphate (35 mg; 0.073 mmol; 7%).

LCMS: Column: XBridge C8 (50×4.6 mm×3.5 μm); Mobile phase: A: 10 mM $NH_4CO_3$ in $H_2O$; B: ACN; RT: 3.11; Purity: (Max: 93.56); M+H: 482.0.

HPLC: Column: XBridge C8 (50×4.6 mm×3.5 μm); Mobile phase: A: 0.1% TFA in $H_2O$; B: ACN; RT: 2.55; Purity: (Max: 96.39; 254 nm: 96.57).

1HNMR (DMSO-$d_6$-$D_2O$ exchange): δ 7.84 (d, J=7.20 Hz, 1H), 7.71-7.70 (m, 1H), 7.65-7.62 (m, 1H), 7.59-7.55 (m, 1H), 7.07 (s, 1H), 6.62 (s, 1H), 4.12 (s, 1H), 3.60-3.54 (m, 1H), 3.30-3.26 (m, 3H), 3.13-3.11 (m, 2H), 2.71 (s, 3H), 1.83-1.80 (m, 1H).

Example 2

Pharmacokinetic Profile of Alvocidib Prodrugs

The following compounds were prepared and their pharmacokinetic profile determined and compared to the pharmacokinetic profile of compound (IB') as described below.

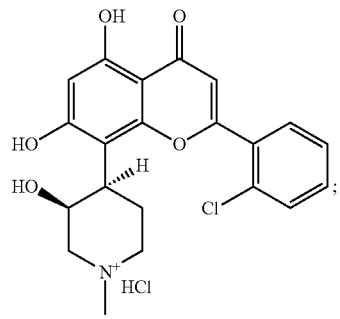
A

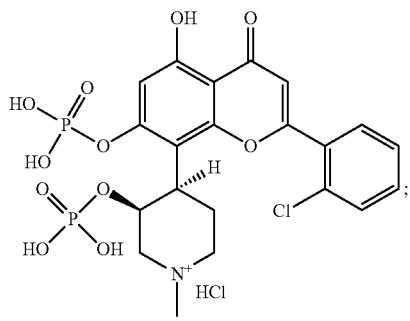
C

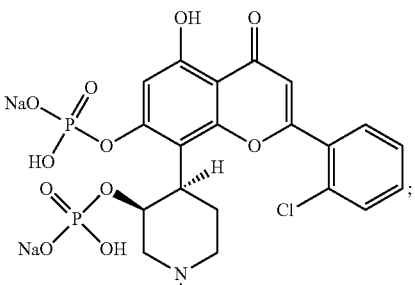
D

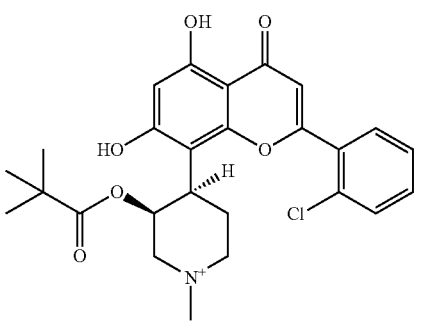
E
and

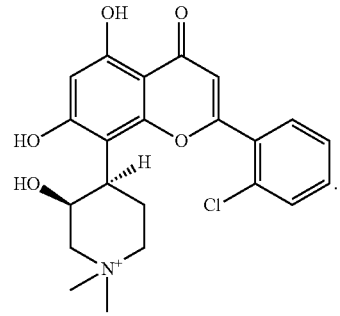
F

Compounds were prepared and administered to CD-1 mice intravenously (IV) or orally (PO) as summarized in Table 1. The plasma concentration of the alvocidib parent compound was determined at various time intervals (Table 2) and the pharmacokinetic parameters calculated (Table 3). Compounds E and F did not convert to alvocidib in vivo (i.e., no alvocidib was detected in plasma samples of mice treated with these compounds), and their pharmacokinetic parameters were not further investigated. As can be seen in Table 3, the bioavailability of compound (IB') is superior that of the parent alvocidib compound (A) and the two diphosphate compounds (C and D).

TABLE 1

Design of Pharmacokinetic Profiling Experiments

|  | IV | PO |
|---|---|---|
| Dose (mg/kg) | 1 | 10 |
| Dosing volume (ml/kg) | 2 | 10 |
| Formulation Conc (mg/ml) | 0.5 | 1 |

TABLE 1-continued

Design of Pharmacokinetic Profiling Experiments

|  | IV | PO |
|---|---|---|
| Formulation Details | | |
| IV Formulation | N-methyl pyrollidone:Ethanol:PEG200:NS (2:10:30:58) | |
| PO Formulation | Tween80:Ethanol:PEG400:water (2:10:30:58) | |
| Type of PK Planed | | |
| Species | Mouse | |
| Strain | ICR-CD1 | |
| Sex | Male | |
| Age/Body weight: | ~7-8 weeks/25-30 g | |
| Groups | IV: 1 gr; PO: 1 gr | |
| No of animals/group | 3/3 | |
| IV Dosing | Tail vein | |
| PO Dosing | oral gvage | |
| Sample Type | Plasma | |
| Blood collection | Saphenous vein | |
| Anti-coagulant used | 0.2% K2 EDTA | |

TABLE 2

Plasma Concentration of Alvocidib

Alvocidib Plasma Concentrations (ng/ml)

| Time (hr) | A | | C | | D | | (IB') | |
|---|---|---|---|---|---|---|---|---|
|  | IV | PO | IV | PO | IV | PO | IV | PO |
| 0.083 | 427.9 ± 26.5 | — | 30.1 ± 6.5 | — | 9.9 ± 8.0 | — | 366.8 ± 9.9 | — |
| 0.25 | 335.7 ± 64.1 | 1491 ± 211.0 | 53.4 ± 11.0 | 7.5 ± 4.2 | 31.4 ± 17.0 | 5.2 ± 4.7 | 265.1 ± 36.4 | 1868.7 ± 51.1 |
| 0.5 | 263.9 ± 48.2 | 1167.2 ± 186.0 | 62.1 ± 2.3 | 17.9 ± 1.0 | 43.8 ± 11.0 | 14.4 ± 1.8 | 183.6 ± 12.5 | 1880.5 ± 119.1 |
| 1.0 | 136.4 ± 41.9 | 675.5 ± 139.7 | 33.2 ± 15.1 | 28.5 ± 2.3 | 45.3 ± 7.2 | 39.3 ± 1.9 | 105.0 ± 17.8 | 1338.5 ± 188.8 |
| 2.0 | 52.5 ± 8.1 | 333.7 ± 94.5 | 19.8 ± 5.34 | 46.0 ± 3.8 | 17.0 ± 5.4 | 59.5 ± 5.9 | 40.2 ± 1.9 | 740.5 ± 147.4 |
| 4.0 | 28.9 ± 6.3 | 304.8 ± 29.5 | 13.5 ± 2.0 | 36.8 ± 1.7 | 9.4 ± 0.7 | 55.5 ± 3.6 | 16.8 ± 1.1 | 388.3 ± 35.7 |
| 6.0 | 13.5 ± 3.3 | 341.3 ± 53.3 | 5.9 ± 0.4 | 100 ± 4.5 | 4.4 ± 0.2 | 108.3 ± 1.4 | 7.22 ± 0.3 | 470.7 ± 18.4 |
| 8.0 | 6.7 ± 0.4 | 241.9 ± 24.9 | 3.6 ± 0.6 | 76.8 ± 3.3 | 2.2 ± 1.6 | 93.1 ± 3.7 | 2.9 ± 0.4 | 252.5 ± 31.0 |
| 24.0 | n.e. | 36.7 ± 11.1 | n.e. | 2.0 ± 0.3 | n.e. | n.e. | n.e. | 21.7 ± 17.5 |

Note:
Results are expressed in Mean ± SD,
n = 3animals/group
n.e. = not evaluated

TABLE 3

Pharmacokinetic Profiles
Mice PK summary Table (Dose: IV-1 mg/kg & PO-10 mg/kg)

| PK Parameters | A IV | A PO | C IV | C PO | D IV | D PO | (IB') IV | (IB') PO |
|---|---|---|---|---|---|---|---|---|
| $C_{max}$ (ng/mL) | — | 1492.0 ± 211.0 | — | 100.1 ± 4.5 | — | 108.3 ± 1.4 | — | 1922.7 ± 72.1 |
| $T_{max}$ (h) | — | 0.25 ± 0.0 | — | 6.0 ± 0.1 | — | 6.0 ± 0.1 | — | 0.33 ± 0.14 |
| $AUC_{Last}$ (ng*h/mL) | 498.0 ± 46.0 | 5034.1 ± 145.6 | 132.8 ± 14.8 | 776.6 ± 32.8 | 109.0 ± 12.0 | 545.8 ± 11.9 | 363.6 ± 18.0 | 6619.6 ± 631.7 |
| $AUC_{0-\infty}$ (ng*h/mL) | 517.0 ± 47.0 | 5341.1 ± 274.2 | 144.6 ± 13.4 | 785.6 ± 33.5 | 114.3 ± 7.0 | — | 370.2 ± 19.0 | — |
| Clearance (L/h/Kg) | 1.9 ± 0.2 | — | 7.0 ± 0.7 | — | 8.8 ± 0.5 | — | 2.7 ± 0.14 | — |
| Vd (L/Kg) | 5.5 ± 1.2 | — | 22.0 ± 5.1 | — | 22.0 ± 13.1 | — | 6.1 ± 0.0 | — |
| $Vd_{SS}$ (L/Kg) | 3.8 ± 0.6 | — | 21.6 ± 4.4 | — | 23.5 ± 7.4 | — | 4.2 ± 0.1 | — |
| Half life (h) | 2.0 ± 0.4 | 5.7 ± 0.7 | 2.2 ± 0.5 | 3.1 ± 0.1 | 1.72 ± 0.9 | — | 1.57 ± 0.08 | 4.4 ± 1.3 |
| Bioavail. (% F) | | 102 ± 11.7 | | 59.0 ± 8.0 | | 50.5 ± 4.7 | — | 182.3 ± 20.0 |

NOTE:
RESULTS ARE EXPRESSED IN MEAN ± SD,
N = 3ANIMALS/GROUPEXAMPLE 3

Kinetic Solubility Profiles

The aqueous kinetic solubility of compound IB' was determined across a broad pH range (i.e. pH 2.2-pH 8.7) and compared to the aqueous kinetic solubility of alvocidib for the same pH range. The solubility of compound IB' was found to be in excess of 1 mg/mL at the lowest pH tested (pH 2.2), rising to above 5 mg/mL at pH 6.8 and pH 8.7. By comparison, the solubility of alvocidib is above 1 mg/mL at pH 2.2 and pH 4.5 but drops to 0.02 mg/mL at pH 6.8 and pH 8.7.

TABLE 4

Kinetic Solubility Profiles

| Compound | Concentration tested (mg/mL) | Solubility (mg/mL) pH 2.2 | pH 4.5 | pH 6.8 | pH 8.7 |
|---|---|---|---|---|---|
| Alvocidib | 1 | 1.05 | 0.95 | 0.02 | 0.00 |
| | 5 | 4.82 | 1.99 | 0.02 | 0.02 |
| | 10 | 4.38 | 1.25 | 0.02 | 0.02 |

TABLE 4-continued

Kinetic Solubility Profiles

| Compound | Concentration tested (mg/mL) | Solubility (mg/mL) pH 2.2 | pH 4.5 | pH 6.8 | pH 8.7 |
|---|---|---|---|---|---|
| Compound IB' | 1 | 1.07 | 1.10 | 1.09 | 1.09 |
| | 5 | 1.90 | 2.33 | 5.56 | 5.65 |
| | 10 | 1.52 | 1.81 | 9.48 | 9.31 |

Example 4

Plasma Stability Profiles

The plasma stability of compound IB' was determined using plasma from four species. Results for mouse, rat, dog and human are shown in Tables 5, 6, 7 and 8 respectively. Alvocidib and flumazenil were used as controls. In mouse, rat and human plasma, compound IB' maintained 100% stability after 5 hour incubation. In dog plasma, approximately 90% of compound IB' remained after 5 hours. By comparison, alvocidib maintained 100% stability across all four species after 5 hours, and flumazenil was unstable in mouse and rat plasma.

TABLE 5

Mouse Plasma Stability Profiles

| Compound | 0 hours | 0.5 hours | 1 hour | 2 hours | 3 hours | 4 hours | 5 hours |
|---|---|---|---|---|---|---|---|
| Flumazenil | 100.00 | 29.96 | 10.21 | 1.56 | 0.39 | 0.20 | 0.07 |
| Alvocidib | 100.00 | 93.58 | 103.12 | 97.19 | 117.38 | 115.72 | 111.28 |
| Compound IB' | 100.00 | 88.48 | 89.83 | 97.71 | 99.61 | 100.46 | 100.20 |

% Remaining

TABLE 6

Rat Plasma Stability Profiles

| | % Remaining | | | | | | |
|---|---|---|---|---|---|---|---|
| Compound | 0 hours | 0.5 hours | 1 hour | 2 hours | 3 hours | 4 hours | 5 hours |
| Flumazenil | 100.00 | 42.23 | 16.13 | 1.69 | 0.23 | 0.00 | 0.00 |
| Alvocidib | 100.00 | 93.12 | 90.20 | 99.31 | 98.69 | 92.57 | 117.71 |
| Compound IB' | 100.00 | 97.39 | 94.60 | 100.04 | 107.48 | 100.20 | 99.78 |

TABLE 7

Dog Plasma Stability Profiles

| | % Remaining | | | | | | |
|---|---|---|---|---|---|---|---|
| Compound | 0 hours | 0.5 hours | 1 hour | 2 hours | 3 hours | 4 hours | 5 hours |
| Flumazenil | 100.00 | 91.80 | 92.00 | 100.99 | 115.10 | 99.44 | 100.53 |
| Alvocidib | 100.00 | 96.41 | 89.16 | 105.76 | 105.84 | 97.65 | 100.40 |
| Compound IB' | 100.00 | 83.66 | 94.53 | 112.61 | 99.16 | 93.91 | 90.24 |

TABLE 8

Human Plasma Stability Profiles

| | % Remaining | | | | | | |
|---|---|---|---|---|---|---|---|
| Compound | 0 hours | 0.5 hours | 1 hour | 2 hours | 3 hours | 4 hours | 5 hours |
| Flumazenil | 100.00 | 96.56 | 90.83 | 92.41 | 117.98 | 95.32 | 94.63 |
| Alvocidib | 100.00 | 92.61 | 93.54 | 93.29 | 111.62 | 100.25 | 104.65 |
| Compound IB' | 100.00 | 96.32 | 88.01 | 104.22 | 102.59 | 94.36 | 100.26 |

Example 5

Pharmacokinetics in Sprague Dawley Rats

The plasma concentrations of alvocidib produced by oral and intravenous (IV) administration of compound IB' and of absorbed compound IB' itself, were determined in male Sprague Dawley (SD) rats (see FIG. 1). Plasma samples were taken at 8 time-points (IV) or 7 time points (oral) over a 24 hour period following a single dose of compound IB' (3 animals per group). The calculated pharmacokinetic parameters are shown in Table 9 and Table 10. Both IV and oral administration of compound IB' led to significant exposure of alvocidib. Administered intravenously, compound IB' (1 mg/kg) was metabolized to alvocidib with a $C_0$ of 270.3 ng/mL which was eliminated with a half-life of 1.6 hours. Administered orally, compound IB' (10 mg/kg) was metabolized to alvocidib with a $C_{max}$ of 178.6 ng/mL and a $T_{max}$ of 2.92 hours, which was eliminated with a half-life of 4.4 hours. The bioavailability of alvocidib (99.03%) was calculated from the ratio of the area under the curve (AUC) for alvocidib produced from oral and IV administration of compound IB'. The plasma samples were also analyzed for the presence of compound IB'. The plasma concentrations of compound IB' in SD rats are also shown in FIG. 1 and Table 11. For both IV and oral administration in SD rats, plasma levels of compound IB' dropped below quantitative levels at 2 hours post dosing.

TABLE 9

Pharmacokinetic Parameters for Alvocidib Following Intravenous Administration of Compound IB' in Sprague Dawley Rats

| Parameter | Value | SD |
|---|---|---|
| $C_0$ (ng/mL) | 270.3 | 48.6 |
| $AUC_{in}$ (hr · ng/mL) | 135.6 | 21.1 |
| $AUC_{0-t}$ (hr · ng/mL) | 129.9 | 22.8 |
| $AUC_{in}/AUC_{0-t}$ (%) | 104.6 | 2.3 |
| $V_d$ (L/kg) | 17.50 | 1.93 |
| $CL_p$ (L/hr/kg) | 7.5 | 1.1 |
| $V_{d,ss}$ (L/kg) | 17.71 | 10.08 |
| $MRT_{in}$ (hr) | 2.5 | 1.8 |
| $t_{1/2}$ (hr) | 1.6 | 0.4 |

TABLE 10

Pharmacokinetic Parameters for Alvocidib Following Oral Administration of Compound IB' in Sprague Dawley Rats

| Parameter | Value | SD |
|---|---|---|
| $C_{max}$ (ng/mL) | 178.6 | 47 |
| $T_{max}$ (hr) | 2.92 | 4.4 |
| $AUC_{in}$ (hr · ng/mL) | 1280.5 | 194 |
| $AUC_{0-t}$ (hr · ng/mL) | 1241.2 | 185 |

TABLE 10-continued

Pharmacokinetic Parameters for Alvocidib Following
Oral Administration of Compound IB' in Sprague
Dawley Rats

| Parameter | Value | SD |
|---|---|---|
| $AUC_{in}/AUC_{0-t}$ (%) | 103.2 | 0.8 |
| Bioavailability (%) | 99.03 | 30.2 |
| $t_{1/2}$ (hr) | 4.40 | 0.5 |

TABLE 11

Plasma Concentrations of Compound IB following
Intravenous or Oral Administration of Compound
IB' in Sprague Dawley Rats

| Time (hr) | IV (ng/mL) | SD | PO (ng/mL) | SD |
|---|---|---|---|---|
| 0.083 | 429.6 | 144.0 | # | # |
| 0.25 | 82.0 | 6.6 | 30.0 | 9.7 |
| 0.50 | 24.6 | 4.2 | 20.4 | 6.6 |
| 1.00 | 9.3 | 2.8 | 9.3 | 0.4 |
| 2.00 | BQL | — | BQL | — |
| 4.00 | BQL | — | BQL | — |
| 6.00 | BQL | — | BQL | — |
| 8.00 | BQL | — | BQL | — |
| 24.00 | BQL | — | BQL | — | not measured
BQL = below quantitation limit

Example 6

Maximum Tolerated Acute Dose in Mice

Figure 2A:
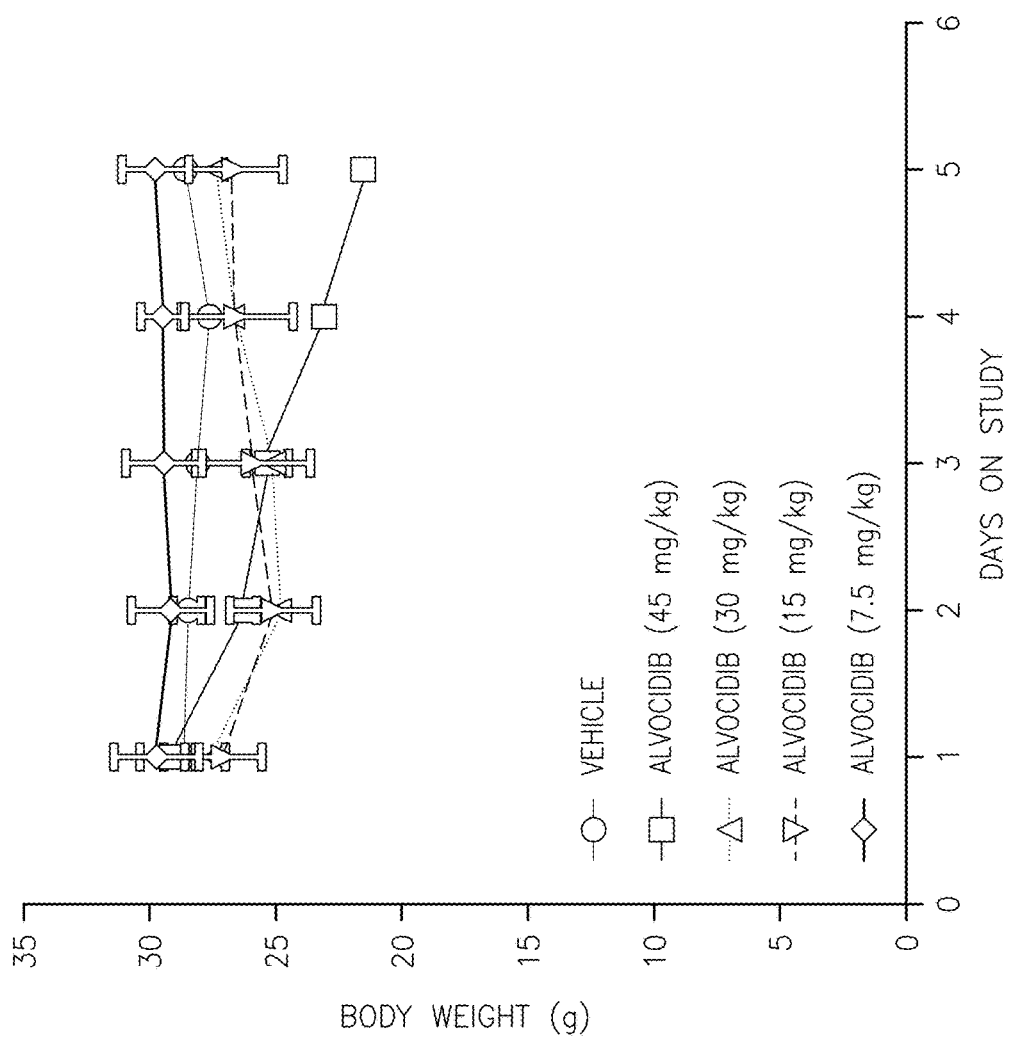
FIG. 2A-D depict the body weights of mice treated with a single dose (FIG. 2A-B orally, FIG. 2C-D intravenously) of alvocidib or compound IB.
Figure 2B:
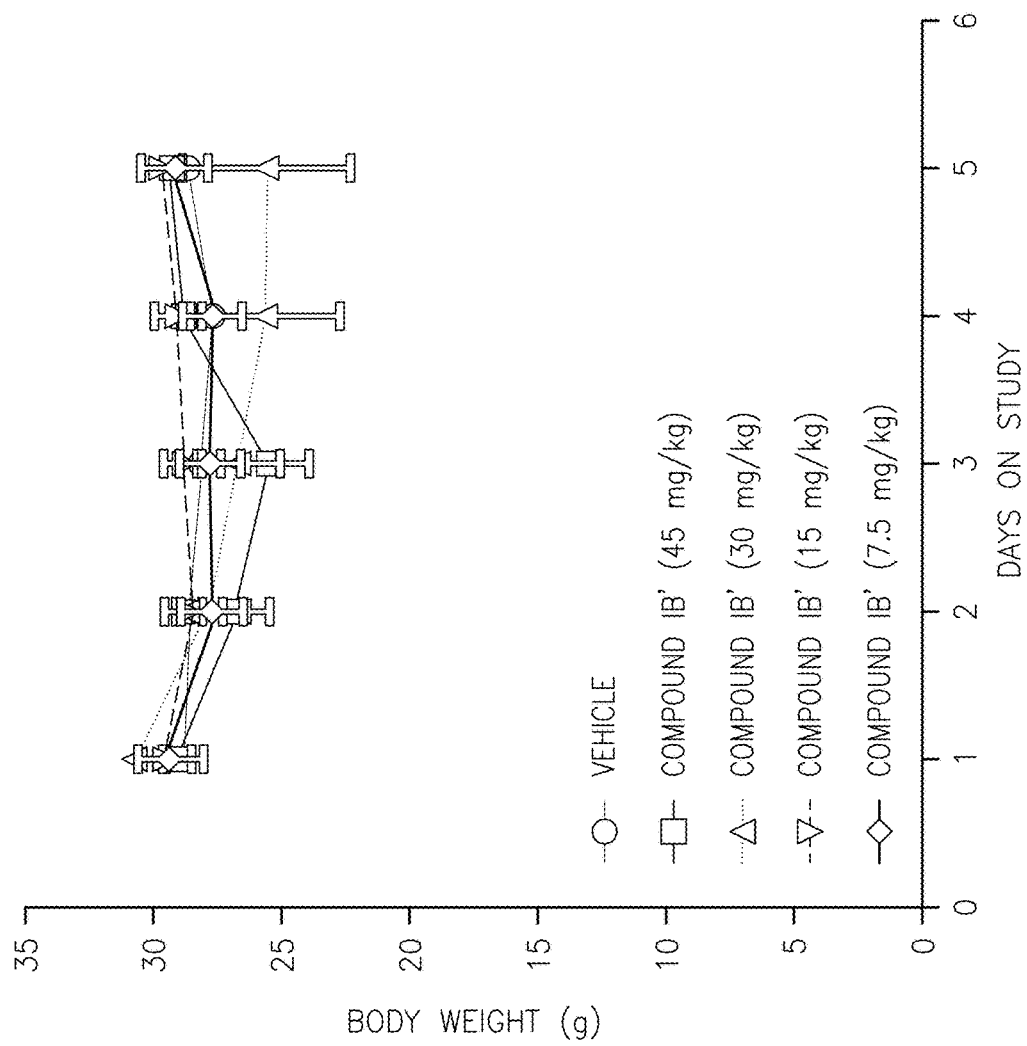
Figure 2C:
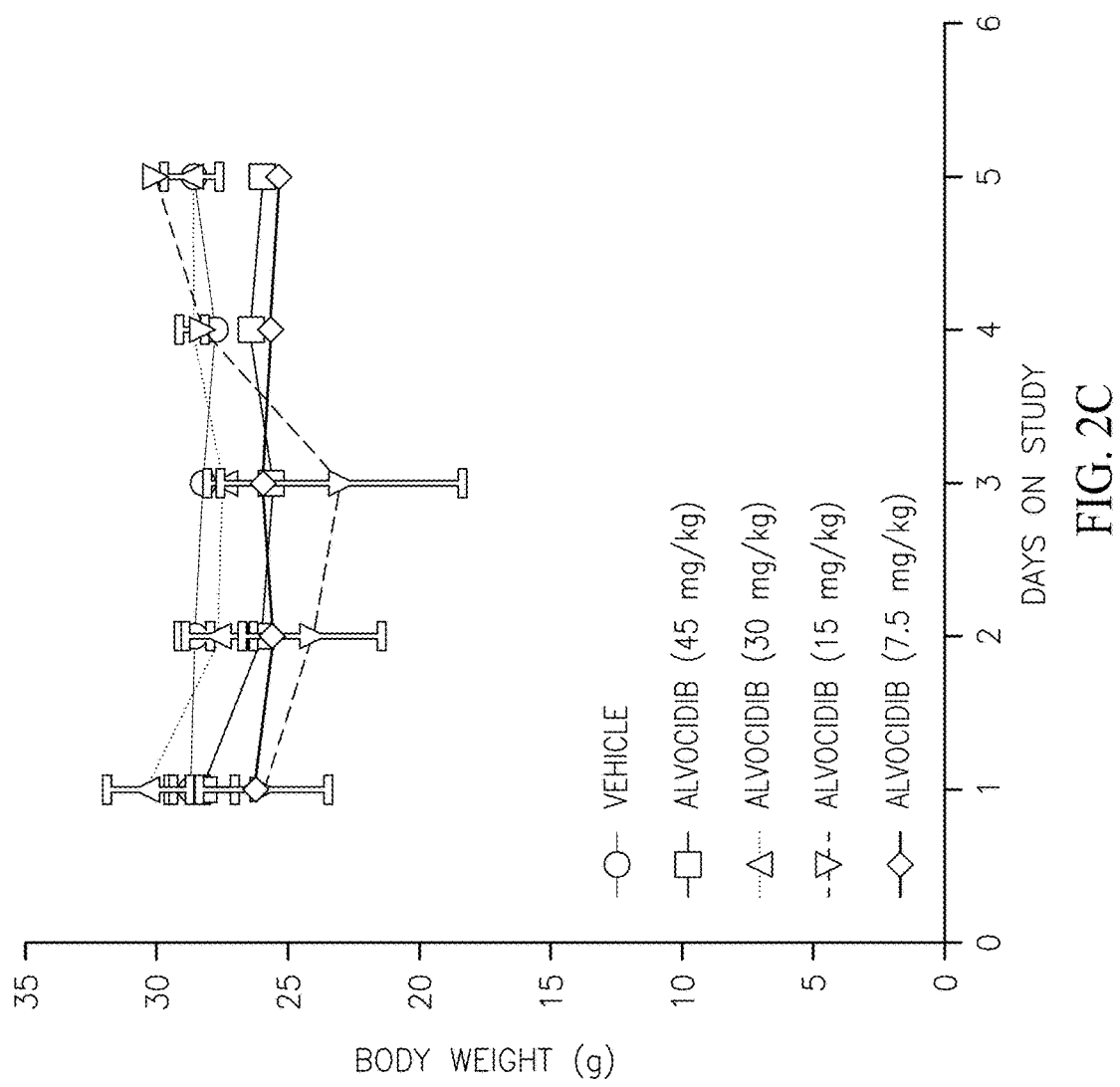
Figure 2D:
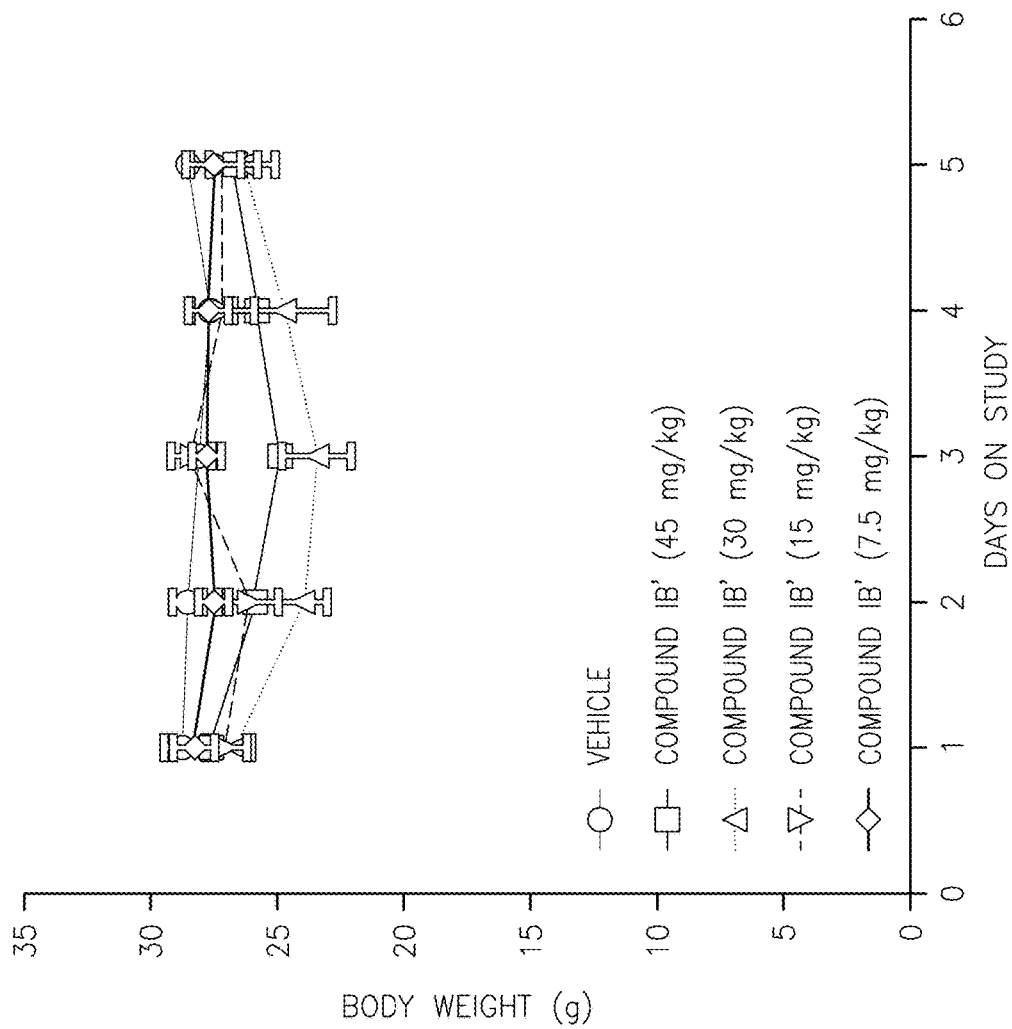

Acute (i.e. single dose) toxicology studies were performed in mice. Acute studies were performed in female SHO SCID mice using three animals per treatment group. Animals were treated with a single dose of compound IB' at 45, 30, 15, or 7.5 mg/kg. For comparison, additional animals were treated with alvocidib at the same dose levels. Body weight measurements following oral dosing (FIGS. 2A-B) and intravenous (IV) dosing (FIG. 2C-D) were used, along with mortality and clinical observations to determine the maximum tolerated acute dose ($MTD_{acute}$).

The results from the acute study determined that the $MTD_{acute}$ of compound IB', dosed orally, is 15 mg/kg. The $MTD_{acute}$ of compound IB', dosed intravenously, is 15 mg/kg. Body weight loss and increased lethargy were observed in animals dosed at 30 mg/kg and 45 mg/kg. In animals dosed orally at 45 mg/kg, one animal died on day two and one animal died on day three. In animals dosed orally at 30 mg/kg, one animal died on day four. In animals dosed intravenously at 45 mg/kg, two animals died on day two. In animals dosed intravenously at 30 mg/kg, one animal died on day three.

The acute $MTD_{acute}$ of alvocidib, when dosed orally, is 15 mg/kg. The $MTD_{acute}$ of alvocidib, dosed intravenously, is 7.5 mg/kg. Some body weight loss, increased lethargy, and animal deaths were observed in animals dosed with alvocidib at both the 30 and 45 mg/kg dose levels.

Body weight loss was observed in surviving animals at 45 mg/kg and 30 mg/kg oral dosing levels of compound IB', peaking at 17% in the 30 mg/kg group. Body weight loss in surviving animals dosed intravenously peaked at 12%.

No overt toxicity was observed in mice dosed orally or intravenously at 15 mg/kg or 7.5 mg/kg. Minor body weight loss peaking at 3.3% in the 15 mg/kg intravenous dosing group was attributed to normal body weight fluctuation in test animals.

Compound IB' is better tolerated ($MTD_{acute}$=15 mg/kg) in mice when dosed intravenously compared to alvocidib ($MTD_{acute}$=7.5 mg/kg).

Example 7

Maximum Tolerated Repeated Dose Schedule in Mice

Figure 3A:
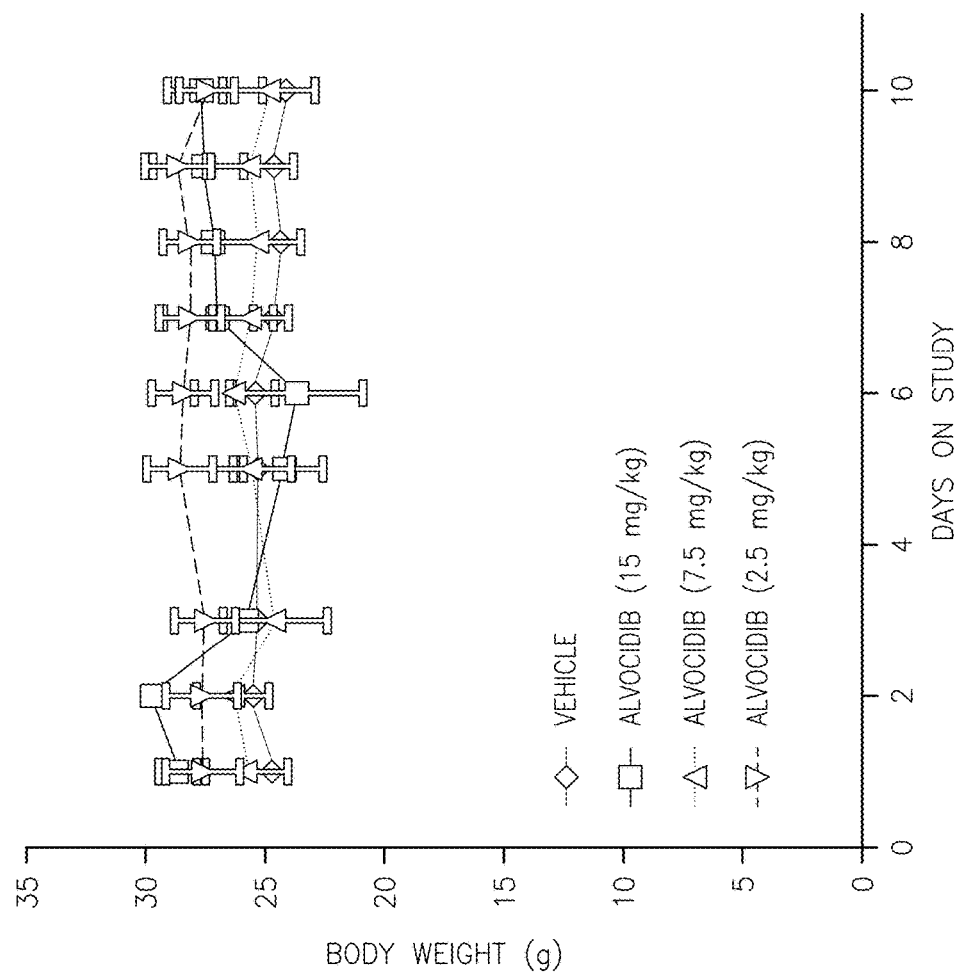
FIG. 3A-D show the body weights of mice treated with daily doses (FIG. 3A-B orally, FIG. 3C-D intravenously) of alvocidib or compound IB.
Figure 3B:
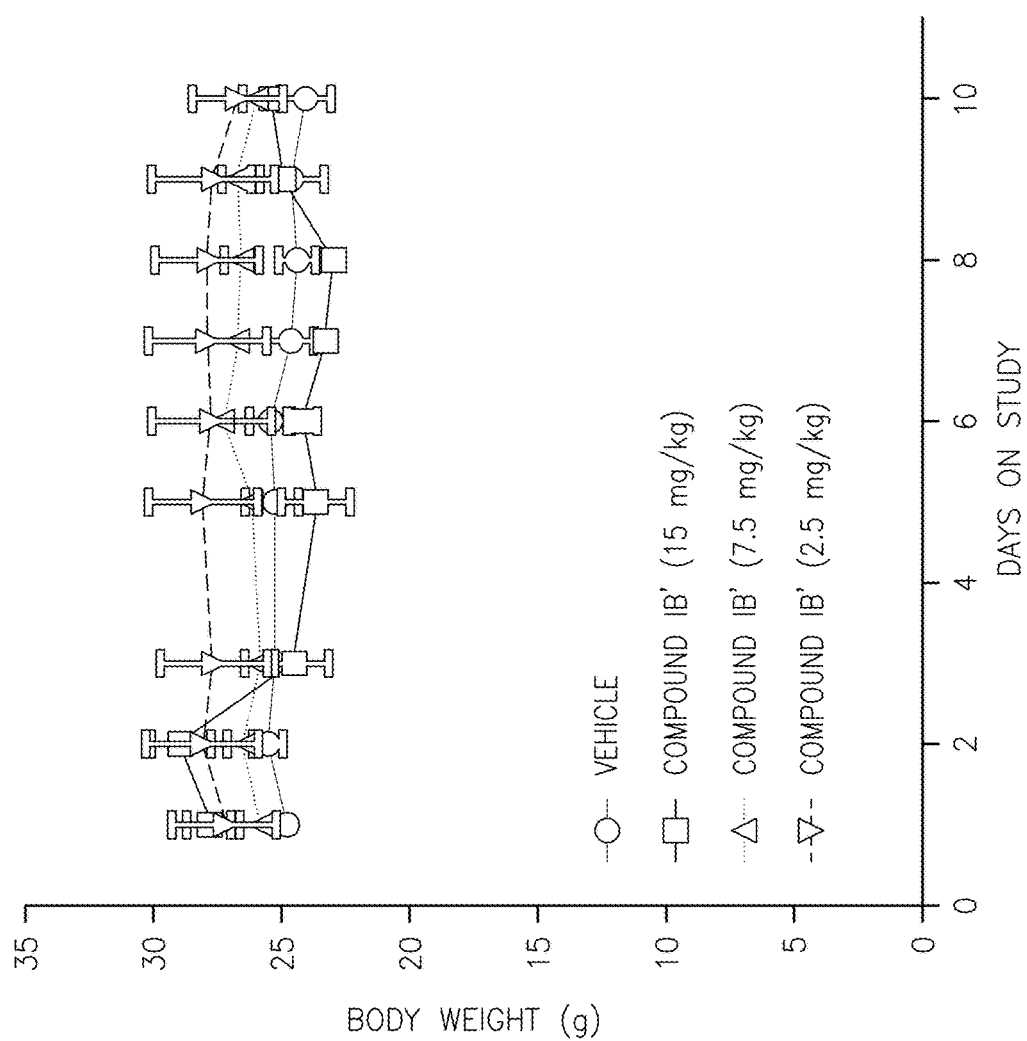
Figure 3C:
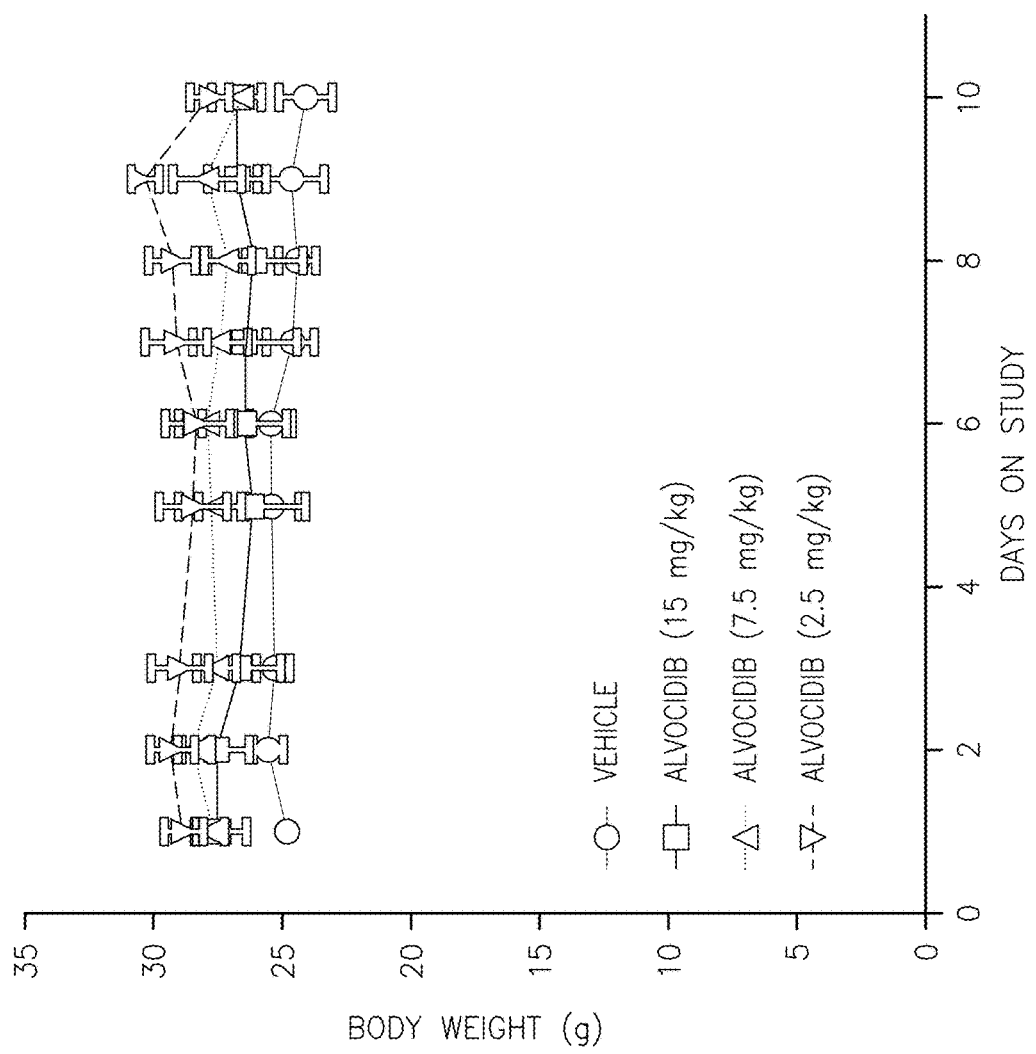
Figure 3D:
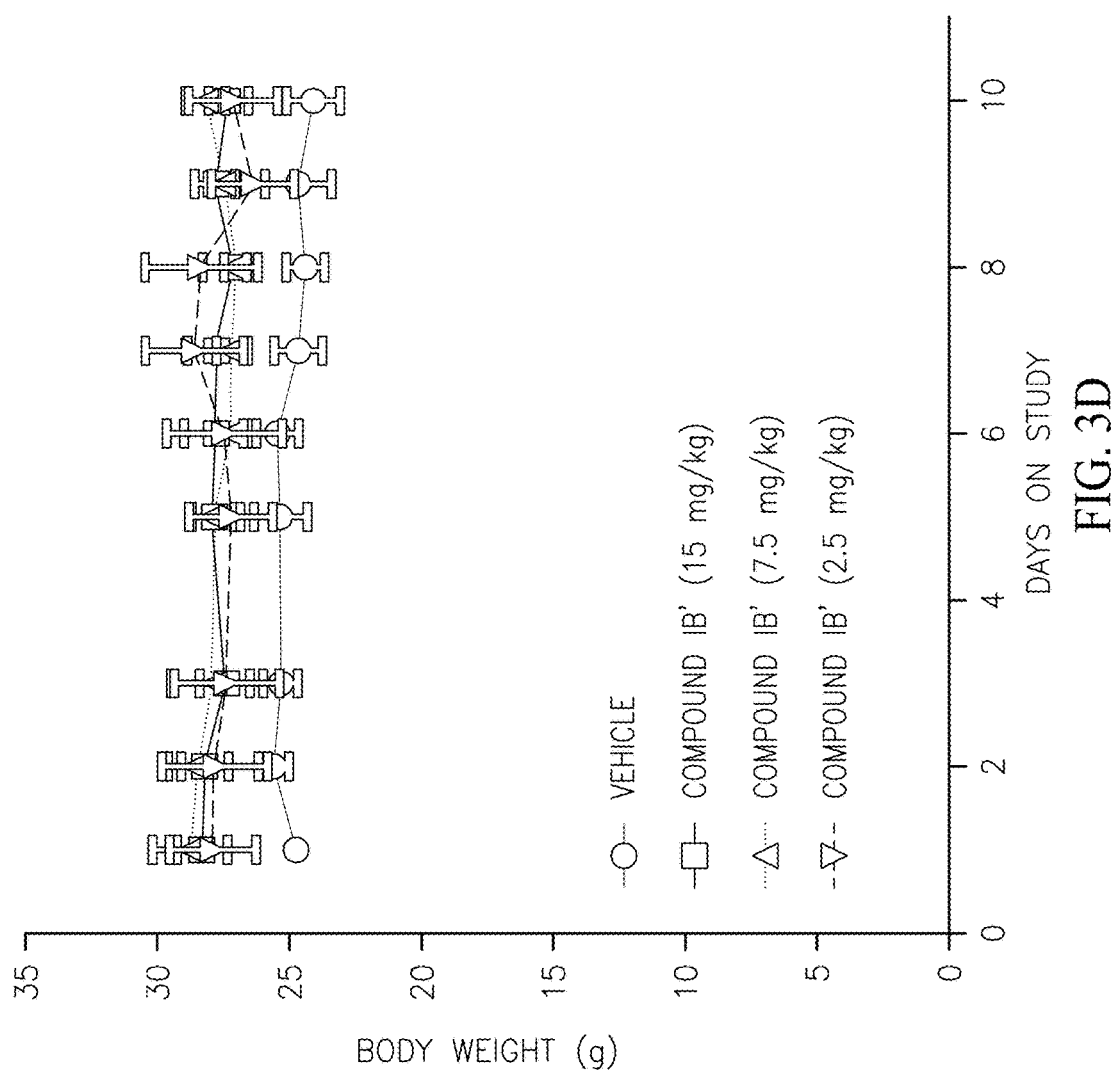

Repeat dose toxicology studies were performed in female SHO SCID mice using 3 animals per treatment group. Animals were treated with five daily doses of compound IB' at 15, 7.5, or 2.5 mg/kg, and were observed for five additional days following the dosing regimen. For comparison, additional animals were treated with alvocidib at the same dose levels and the same dosing/observation schedule. Body weight measurements of animals treated by oral (see FIGS. 3A-B) and intravenous (see FIG. 3C-D) dosing over the course of the 5-day repeat dosing period and subsequent 5-day observation period, along with mortality and clinical observations, were used to determine the maximum tolerated dosing schedule ($MTD_{repeat}$).

The results from the 5-day repeat-dose study determined that the $MTD_{repeat}$ of compound IB, dosed orally, is 7.5 mg/kg. The $MTD_{repeat}$ of compound IB', dosed intravenously, is 15 mg/kg. Body weight loss was observed in animals dosed orally at 15 mg/kg. In animals dosed orally at 15 mg/kg, one animal died on day 5, and one animal died on day 7.

For comparison, the $MTD_{repeat}$ determined for alvocidib, when dosed orally, was 7.5 mg/kg. The $MTD_{repeat}$ determined for alvocidib, when dosed intravenously, was 7.5 mg/kg. Lethargy, body weight loss, and deaths were observed at the 15 mg/kg dosing levels for both oral and intravenous dosing with alvocidib.

Body weight loss was observed in surviving animals at the 15 mg/kg oral dosing level with compound IB', which peaked at 12%. No overt toxicity was observed in animals dosed orally at 7.5 mg/kg or 2.5 mg/kg, or in animals dosed at any dose level attempted when administered intravenously.

Compound IB' is better tolerated ($MTD_{repeat}$=15 mg/kg) in mice when dosed intravenously compared to alvocidib ($MTD_{repeat}$=7.5 mg/kg).

Example 8

Maximum Tolerated Acute Dose in Rats

Acute (i.e. single dose) toxicology studies were performed in rats. Acute studies were performed in female Sprague Dawley rats using three animals per treatment group. Animals were treated with a single dose of compound IB' at 36, 18, 9, or 4.5 mg/kg. For comparison, additional animals were dosed with 18, 9, or 4.5 mg/kg alvocidib. Body weight measurements following oral dosing (see FIG. 4A), along with mortality, clinical observations, food consumption (see FIG. 4B), and complete blood counts (CBCs; see Table 12) were used to determine the maximum tolerated acute dose ($MTD_{acute}$).

The results from the acute study determined that the $MTD_{acute}$ of compound IB' in rats is 18 mg/kg. Diarrhea, body weight loss and increased lethargy were observed in animals dosed with compound IB at 36 mg/kg. At this dose level, one animal died on day three, one animal died on day four, and one animal died on day 5. Deaths were not observed in any other treatment group.

Figure 4A:
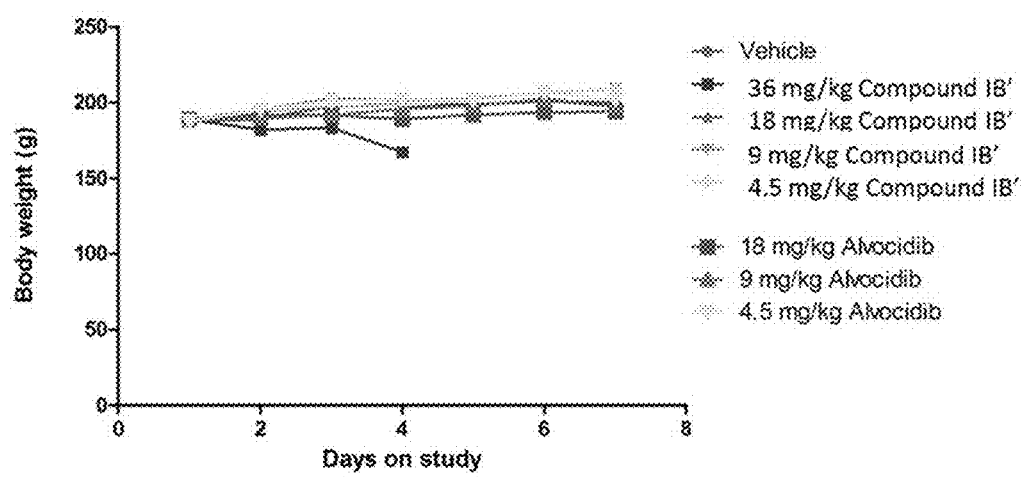
FIG. 4A-B show body weights and food consumption of rats treated with a single dose (orally) of alvocidib or compound IB.
Figure 4B:
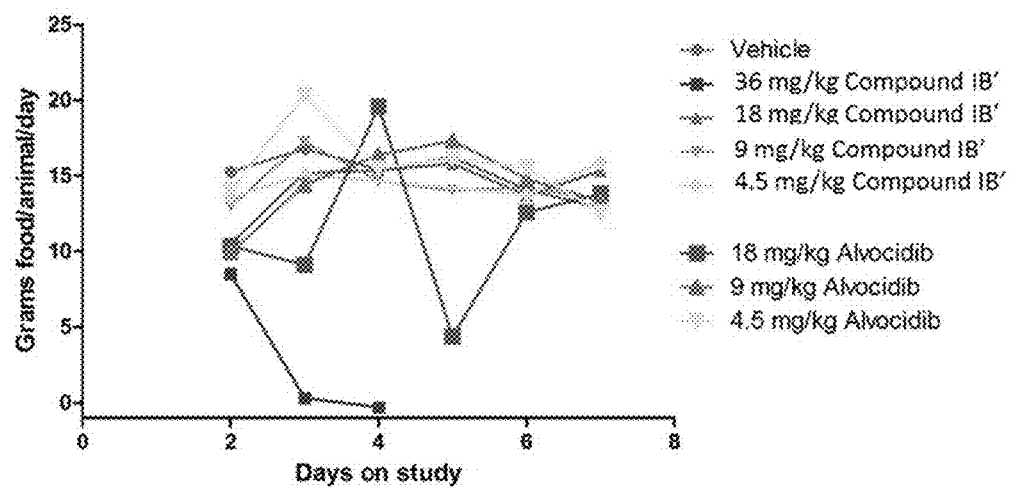

Body weight loss was observed in treated animals, preceding death, reaching 13.1% in animals treated at the 36 mg/kg dose level with compound IB' (see FIG. 4A). This body weight loss was accompanied by significant diarrhea, and increased lethargy in these animals. No overt toxicity, including body weight change or diarrhea, was observed in rats dosed at 18, 9, or 4.5 mg/kg with compound IB'. In comparison, animals dosed with 18 mg/kg alvocidib did show signs of diarrhea. In addition, abnormal food consumption patterns were observed with 18 mg/kg dosing of alvocidib that were not observed with the compound IB' treated animals at the same dosage level.

Abnormal CBCs were observed in some animals (Table 12). Specifically, platelet counts were outside the normal range for the vehicle and 9 mg/kg dosage of compound IB', and 4.5 mg/kg alvocidib dose. No consistent dose-dependent trend was observed in the surviving, treated animals. Slightly reduced red and white blood cell counts were observed at the 18 mg/kg dose level for compound IB'. However, slightly elevated counts were also observed in some untreated animals as well. The high variability of these results was attributed to inter-animal variation, and not drug-dependent mechanisms. As animals treated with 36 mg/kg of compound IB' expired overnight, CBCs were not available.

Based on the data above, the rat oral $MTD_{acute}$ of compound IB' was found to distinguish its tolerability profile versus that of alvocidib as the no observable adverse effect level (NOAEL) was found to be 18 mg/kg for compound IB' and 9 mg/kg for alvocidib.

Figure 5A:
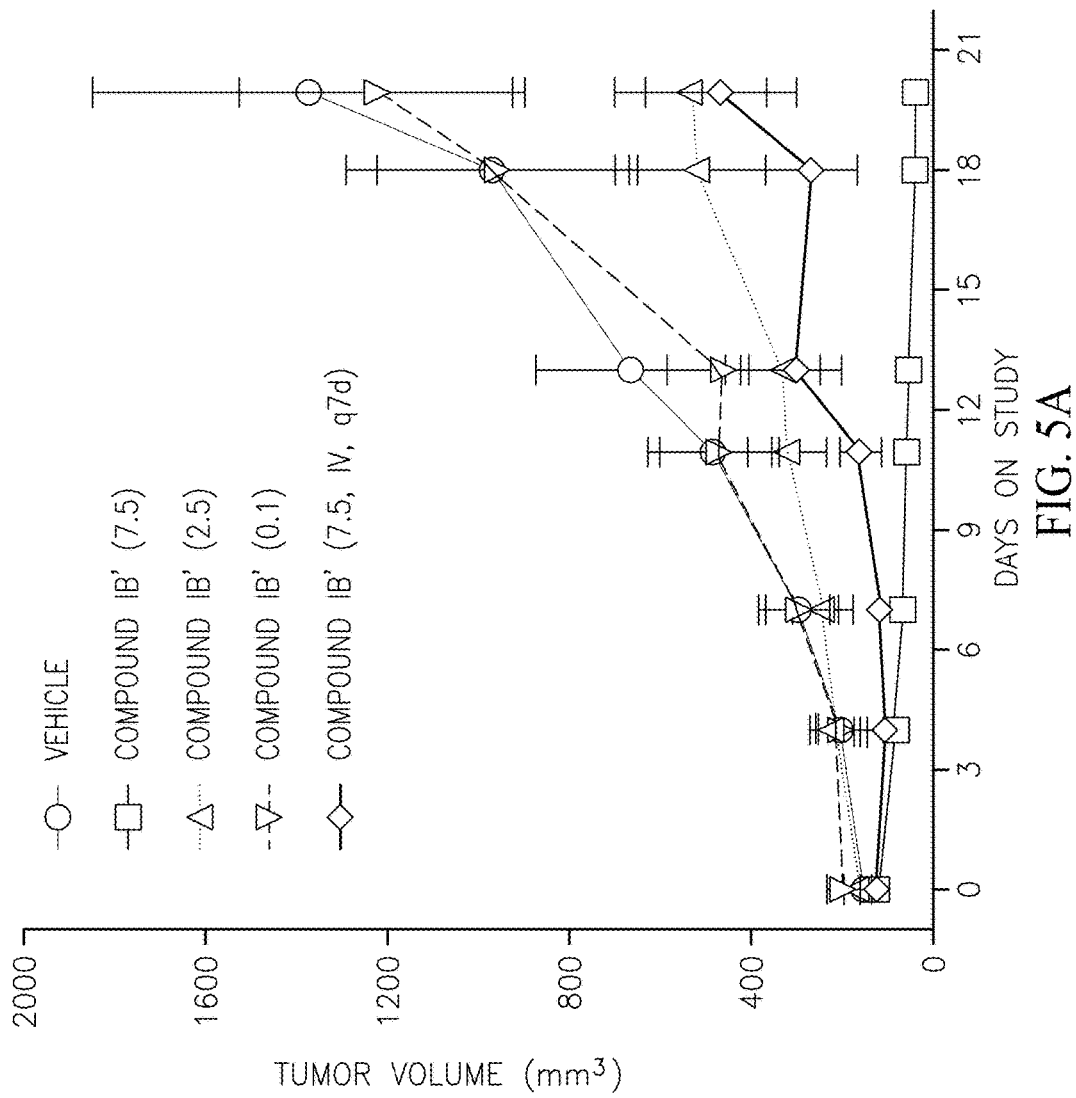
FIG. 5A-B show in vivo tumor volume and body weight after dosing with compound IB during a xenograft efficacy study.
Figure 5B:
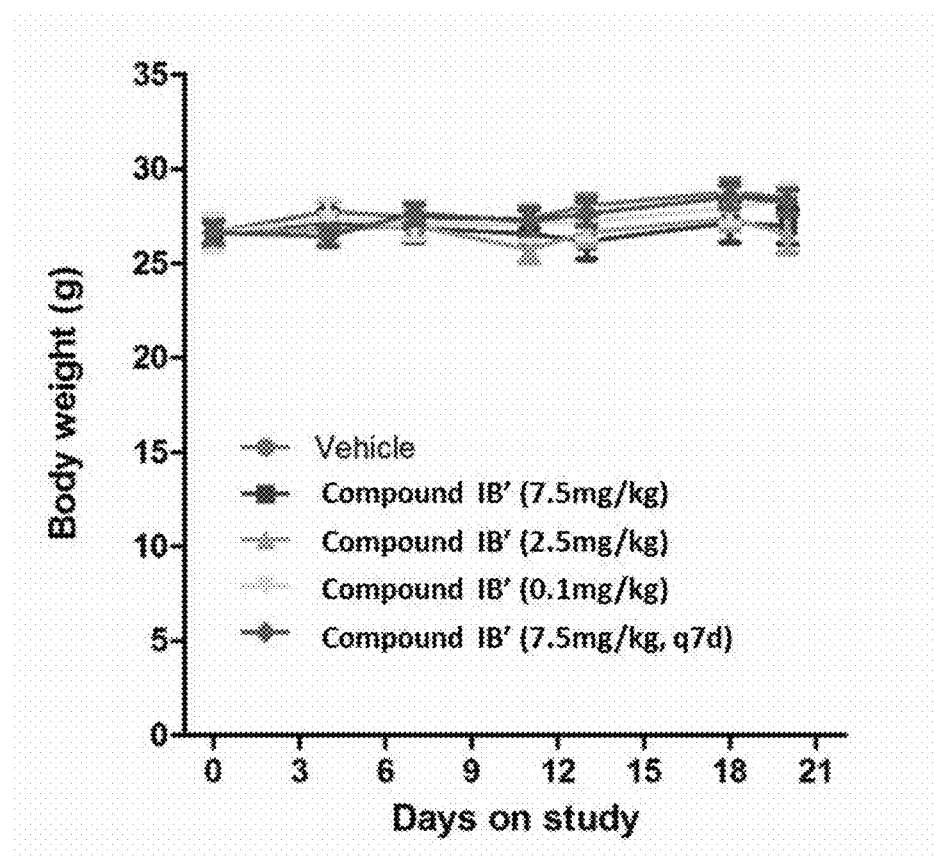

(7.5 mg/kg, q7dx3), which was dosed intravenously. Treatment resulted in significant tumor growth inhibition (% TGI; see FIGS. 5A-B and Table 13).

TABLE 13

Tumor Growth Inhibition for Mouse Xenograft Efficacy Study

| Dosage of Compound IB' | Tumor Growth Inhibition (%) |
|---|---|
| Vehicle (i.e. no compound IB') | 0 |
| 7.5 mg/kg | 69 |
| 2..5 mg/kg | 12 |
| 7.5 mg/kg, q7dx3 | 74 |

Example 10

Mouse Xenograft Pharmacodynamic Study

Figure 6A:
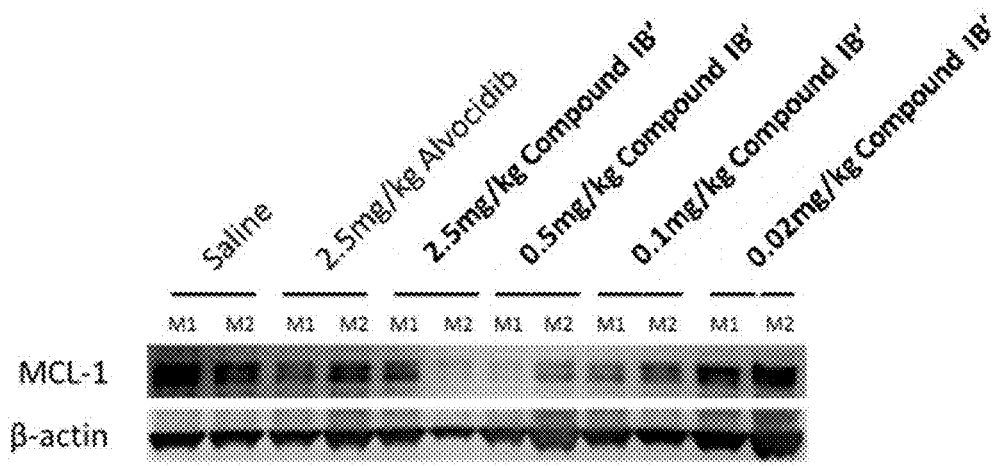
FIG. 6A-B depict reduction of MCL-1 protein expression following treatment with compound IB during a xenograft pharmacodynamic study.
Figure 6B:
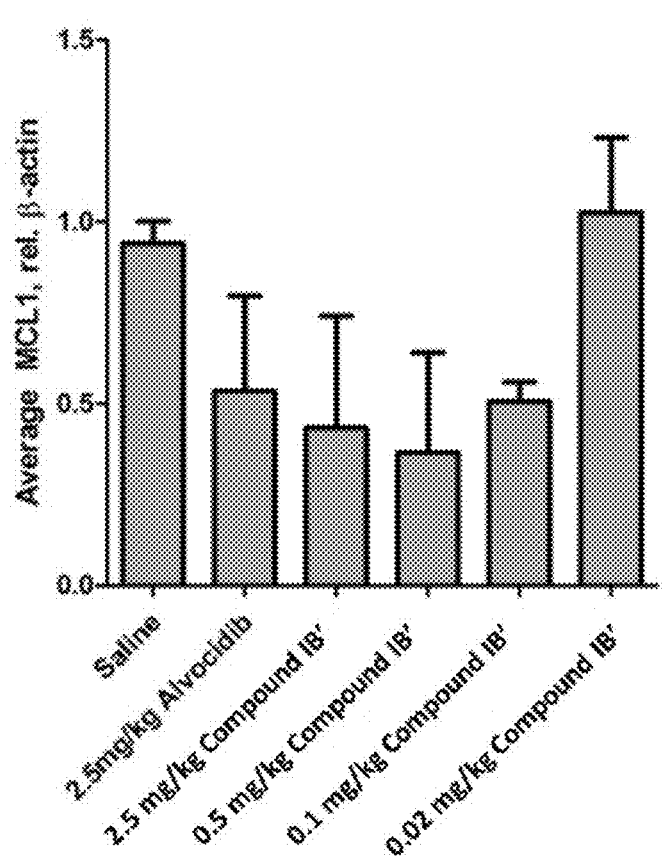

The in vivo pharmacodynamic activity of compound IB' was determined in a MV4-11 mouse xenograft model of AML (FIG. 6A-B). Injection of $8 \times 10^6$ cells/mouse was followed by growth of tumors to approximately 100 mm$^3$. After tumors reached an appropriate size, mice were randomized into the following treatment groups: Vehicle, compound IB' (2.5 mg/kg), compound IB' (0.5 mg/kg), compound IB' (0.1 mg/kg), compound IB' (0.02 mg/kg). Mice were administered a single treatment dose and tumors were harvested 48 hours post-treatment. MCL-1 protein levels were assessed on harvested tumors using standard polyacrylamide gel electrophoresis and immunoblotting technique (FIG. 6A). Treatment resulted in reduction of MCL-1 protein expression (see FIG. 6B and Table 14 below).

TABLE 12

Blood Counts of Rats Treated With a Single Dose of Compound IB

| | RBC ($10^6$/μL) | MCV (fL) | HCT (%) | MCH (pg) | MCHC (g/dL) | RDWA (fL) | PLT ($10^3$/μL) | HGB (g/dL) | WBC ($10^3$/μL) |
|---|---|---|---|---|---|---|---|---|---|
| Vehicle | 7.8 | 53.1 | 41.5 | 19.5 | 36.8 | 15.7 | 34.3 | 174.3 | 15.2 |
| 36 mg/kg compound IB' | — | — | — | — | — | — | — | — | — |
| 18 mg/kg compound IB' | 5.9 | 53.5 | 31.2 | 19.6 | 36.6 | 15.7 | 33.9 | 201.3 | 11.4 |
| 9 mg/kg compound IB' | 8.0 | 53.3 | 42.7 | 19.5 | 36.6 | 15.9 | 35.0 | 112.7 | 15.6 |
| 4.5 mg/kg compound IB' | 9.1 | 54.8 | 49.9 | 19.7 | 35.9 | 16.2 | 37.1 | 319.3 | 17.9 |
| 18 mg/kg alvocidib | 8.8 | 53.8 | 47.3 | 19.3 | 35.9 | 16.1 | 36.1 | 376.0 | 16.9 |
| 9 mg/kg alvocidib | 8.7 | 54.0 | 47.1 | 19.3 | 35.7 | 16.2 | 36.3 | 334.7 | 16.8 |
| 4.5 mg/kg alvocidib | 8.3 | 52.7 | 43.6 | 18.7 | 35.4 | 16.0 | 34.7 | 147.0 | 15.4 |

Example 9

Mouse Xenograft Efficacy Study

The in vivo activity of compound IB' was determined in a MV4-11 mouse xenograft model of acute myeloid leukemia (AML). Injection of $8 \times 10^6$ MV4-11 cells/mouse was followed by growth of tumors to approximately 100 mm$^3$. After tumors reached the appropriate size, mice were randomized into the following treatment groups: Vehicle, compound IB' (7.5 mg/kg, qdx5x3), compound IB' (2.5 mg/kg, qdx5x3), compound IB' (0.1 mg/kg, qdx5x3) and compound IB (7.5 mg/kg, q7dx3). Vehicle and compound IB' were administered orally, except in the last arm of compound IB'

TABLE 14

Reduction of MCL-1 Protein Expression

| Dosage of Compound IB' | Reduction of MCL-1 Expression (%) |
|---|---|
| Vehicle (i.e. no compound IB') | 0.0 |
| 2.5 mg/kg | 54 |
| 0.5 mg/kg | 61 |
| 0.1 mg/kg | 46 |
| 0.02 mg/kg | 0.0 |

All of the U.S. patents, U.S. patent application publications, U.S. patent applications, foreign patents, foreign patent applications and non-patent publications referred to in this specification, including U.S. Provisional Patent Application Ser. No. 62/163,188, filed May 18, 2015, are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A method for treating a hematologic cancer in a mammal in need thereof, the method comprising administering a therapeutically effective amount of a pharmaceutical composition comprising a compound of structure (IB'), to the mammal, wherein the compound of structure (IB') has following structure:

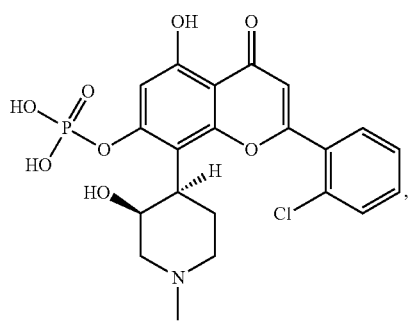

or a pharmaceutically acceptable salt thereof.

2. The method of claim 1, wherein the hematologic cancer is selected from acute myelogenous leukemia (AML), multiple myeloma, follicular lymphoma, acute lymphoblastic leukemia (ALL), chronic lymphocytic leukemia (CLL) and non-Hodgkin's lymphoma.

3. The method of claim 2, wherein the hematologic cancer is acute myelogenous leukemia (AML).

4. The method of claim 2, wherein the hematologic cancer is chronic lymphocytic leukemia (CLL).

5. The method of claim 1, wherein the hematologic cancer is myelodysplasic syndrome (MDS).

6. The method of claim 1, wherein the method comprises orally administering the pharmaceutical composition comprising the compound of structure (IB') to the mammal.

7. The method of claim 1, wherein the pharmaceutical composition comprises the pharmaceutically acceptable salt of the compound of structure (IB').

8. The method of claim 7, wherein the pharmaceutically acceptable salt is a base addition salt.

9. The method of claim 7, wherein the pharmaceutically acceptable salt is a sodium salt.

10. The method of claim 7, wherein the pharmaceutically acceptable salt is an acid addition salt.

11. The method of claim 7, wherein the pharmaceutically acceptable salt is a hydrochloride salt.

12. The method of claim 1, wherein the hematologic cancer is multiple myeloma.

13. The method of claim 1, further comprising administering to the mammal one or more additional therapeutic agents.

* * * * *